United States Patent
Novak et al.

(10) Patent No.: US 11,827,588 B2
(45) Date of Patent: Nov. 28, 2023

(54) COMPOUND, AGENT AND COMPOSITION FOR THE SUPPRESSION OF CANCER GROWTH

(71) Applicant: Vector Vitale IP LLC, North Miami Beach, FL (US)

(72) Inventors: Peter Novak, Sunny Isles Beach, FL (US); Maxim Temnikov, Miami, FL (US); Oleksandr Balakin, Dnepropetrovsk (UA)

(73) Assignee: Vector Vitale IP LLC, North Miami Beach, FL (US)

( * ) Notice: Subject to any disclaimer, the term of this patent is extended or adjusted under 35 U.S.C. 154(b) by 0 days.

(21) Appl. No.: 17/696,701

(22) Filed: Mar. 16, 2022

(65) Prior Publication Data

US 2022/0220070 A1    Jul. 14, 2022

Related U.S. Application Data

(63) Continuation of application No. 16/972,169, filed as application No. PCT/US2019/034473 on May 29, 2019, now Pat. No. 11,286,236.

(60) Provisional application No. 62/741,318, filed on Oct. 4, 2018, provisional application No. 62/680,584, filed on Jun. 5, 2018.

(51) Int. Cl.
C07C 311/21  (2006.01)
A61P 35/00   (2006.01)

(52) U.S. Cl.
CPC ............ *C07C 311/21* (2013.01); *A61P 35/00* (2018.01)

(58) Field of Classification Search
None
See application file for complete search history.

(56) References Cited

U.S. PATENT DOCUMENTS

2018/0055879 A1    3/2018  Novak et al.

FOREIGN PATENT DOCUMENTS

| EP | 0472053 A2  | 2/1992 |
| JP | 2016083858 A | 5/2016 |

OTHER PUBLICATIONS

International Application No. PCT/US2019/034473, International Search Report and Written Opinion dated Sep. 5, 2019, 8 pages.
Brewer et al. "High PH Therapy for Cancer in Mice and Humans", Microbios Letters, vol. 25, No. 99-100, 1984, pp. 123-130.
International Application No. PCT/US2019/034473, International Preliminary Report dated Dec. 8, 2020, 6 pages.

*Primary Examiner* — Sudhakar Katakam
*Assistant Examiner* — Jennifer C Sawyer
(74) *Attorney, Agent, or Firm* — Liang & Hennessey LLP; Stanley D. Liang

(57) ABSTRACT

Novel $^{85}$Rb-enriched rubidium salt compounds of general formula 1, below and novel compounds of general formula 2, below. Compositions that contain at least one of the novel compounds and optionally further contain an antitumor drug. Methods that entail administering such compounds and compositions to treat cancer, optionally in combination with a conventional form of cancer therapy, such as chemotherapy and radiation treatment. When administered with a conventional form of cancer therapy, the compounds and compositions of the invention may be administered before, simultaneously with, or after administration of the conventional form of cancer therapy.

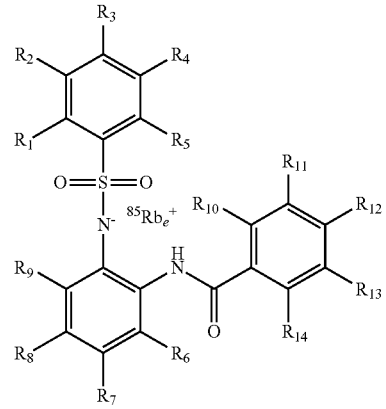

Formula 1

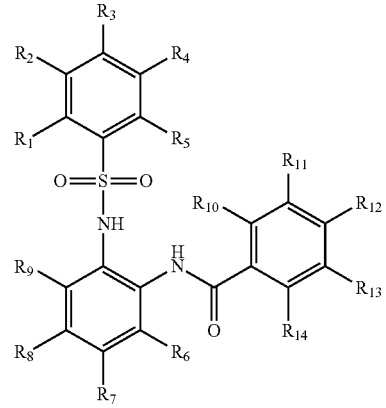

Formula 2

6 Claims, 20 Drawing Sheets

COMPOUND, AGENT AND COMPOSITION FOR THE SUPPRESSION OF CANCER GROWTH

TECHNICAL FIELD OF THE INVENTION

The present invention relates to the field of medicine and pharmacology, and more specifically, to novel methods, compounds and compositions for the treatment of neoplastic diseases, melanoma in particular. The compound of the invention is a rubidium organic salt enriched for $^{85}$Rb that shows antitumor activity. The composition of the present invention comprises the $^{85}$Rb-enriched salt optionally in combination with antitumor agents wherein the combination of components provides a synergistic suppression effect on cancer growth. The claimed compound and composition based on the $^{85}$Rb-enriched organic salt can be used for cancer treatment both individually and in combination with other antitumor therapies. The invention can be used for the effective treatment of malignant diseases as it is characterized by high activity against cancer cells and has a reduced toxic effect on normal cells and the whole organism in general.

BACKGROUND OF THE INVENTION

At present, cancer is the second leading cause of death globally, after cardiovascular diseases. Statistics show that the incidence of oncological diseases is growing every year, and today this problem is one of the greatest challenges for medical and pharmaceutical industries.

Methods of treating cancer include surgery, radiation therapy and chemotherapy. A surgical approach to the treatment of tumors is based on the removal of the tumor burden and is attended by a high risk and stress associated with surgical intervention and postoperative complications. In addition, there is no guarantee that all of the cancer is removed and that metastasis does not occur after removal of the tumor tissue. Surgical removal of the primary tumor without stimulation of the immune system, as a rule, leads to metastasis. Radiation therapy can lead to serious consequences for the patient's body, as it causes genetic damage to normal healthy viable cells, has a carcinogenic effect and inhibits the patient's immune system.

Chemotherapy is another approach used to treat cancer. Chemotherapy is a type of cancer treatment that uses drugs to destroy cancer cells. Some chemotherapeutic drugs can be prescribed in a certain order depending on the type of cancer. Although chemotherapy can be very effective in the treatment of certain types of cancer, chemotherapeutic drugs can adversely affect not only tumor cells but also normal cells. Because of this, side effects are quite common with systemic chemotherapy. A combined use of chemotherapeutic drugs can improve the suppression of tumor growth in a patient, but such combination chemotherapy does not reduce its adverse toxicity to the body. In addition, in many cases, chemotherapy causes severe side effects and carries the risk of suppression of the immune system.

Chemotherapy, in a significant number of cases, also produces severe side effects and carries a risk of suppression of the immune system. In this regard, there is currently a need for innovative methods of treating cancer that would not produce such destructive effects on the patient's body as described above.

An approach that involves the use of light isotopes for the treatment of cancer in humans and animals is a topic for scientific research of worldwide interest and is gaining ground every year. In particular, it has been found out that natural water and most foodstuffs used by man contain heavy isotopes of chemical elements. Each person, being a complex biochemical system, fractionates heavy isotopes throughout his/her life. As a result, accumulation of heavy isotopes in a human body starts from the moment of a person's birth. They gradually "embed" in the cells of the body which leads to a constant decrease in the rate of biological processes. One of the consequences of such accumulation is diminishing of the body's ability to get rid of wastes, toxins and heavy metals which inevitably causes deterioration of health and generally feeling unwell, illnesses become more frequent, old age comes earlier and life shortens. In addition, heavy isotopes embed into DNA and RNA cells and disrupt the work of genetic apparatus of human cells which has a harmful effect on the health of future generations.

A number of works demonstrate that the isotopic composition of tissues and organs may serve as a diagnostic marker. In particular, the study of ratios of Cu and Zn isotopes in blood showed promising interrelationships with age, sex and pathologies. For example, an estimate of the ratio of Cu isotopes in serum is a new approach to the diagnosis and prognosis of the development of cirrhosis (M. Costas-Rodriguez et al., Isotopic analysis of Cu in blood serum by multi-collector ICP-mass spectrometry: a new approach for the diagnosis and prognosis of liver cirrhosis, *Metallomics* 2015, 7. 491-498). The isotopic composition of Zn in breast tissues makes it possible to diagnose cancer (F. Lamer et al., Zinc isotopic compositions of breast cancer tissue, *Metallomics* 2015, 7. 107-112).

Patent application WO2007/140280 proposes an anticancer composition for topical administration comprising cesium ions and/or rubidium ions as pharmaceutically acceptable salts that can be used for the treatment of malignant melanomas. The expediency of using this method is based on an approach that involves changing the acidic pH of cancer cells to a slightly alkaline pH which puts the survival of a cancer cell at risk, and the formation of acidic and toxic materials, which usually occurs in cancer cells, is neutralized and eliminated (Sartori, H E. Nutrients and cancer: an introduction to cesium therapy, Pharmacol. Biochem. Behav. 1984; 21, Suppl. 1: 7-10). Thus mass-spectroscopic and isotopic studies have shown that potassium, rubidium and cesium are absorbed by cancer cells most efficiently. Glucose can still enter the cell, but oxygen cannot. Thus the cell becomes anaerobic. In the absence of oxygen, glucose is fermented to lactic acid, and pH of the cell is reduced to 7 and finally to 6.5. Cesium, rubidium and potassium, which create high pH values, are able to enter cells in this state and increase their pH value. Cesium and rubidium ions can change the ionic physiology of the cancer cell including inhibition of the transmembrane movement of potassium. It is assumed that cesium and rubidium effectively control the flow of potassium and bound hydrogen ion (H+) that affect all acid-dependent cancers and provide affinity to the site to selectively increase the pH of the tumor microenvironment. Without wishing to be bound by theory, the inventors hypothesize that this provides selective tumor modulation and jeopardizes the tumor's existence. The present invention provides, among other things, novel $^{85}$Rb-enriched compounds, a composition for oral administration, a composition for topical administration by itself as stand-alone treatment and provides a composition for intravenous administration as a supplement to cancer therapy, all of which compositions contain the novel $^{85}$Rb-enriched compounds, and methods that entail administering such compositions to treat cancer. In comparison with the state of the art (see, e.g., patent application WO2007/140280), the claimed invention is characterized by high efficiency and produces a systemic effect on the body.

SUMMARY OF THE INVENTION

It is therefore an object of the invention to provide a compound of Formula 1, diagrammed below.

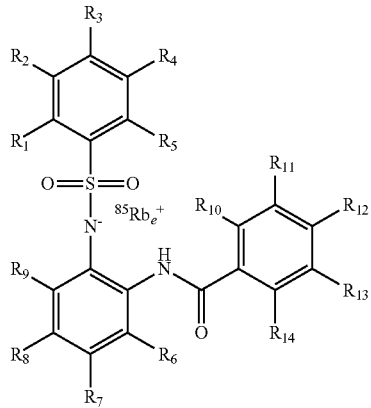

Formula 1

A compound of Formula 1 is a rubidium salt wherein the rubidium is enriched for $^{85}$Rb and wherein each of $R_1$ through $R_{10}$ is independently selected from H, OH, F, Cl, Br, I, $C_1$-$C_6$ alkyl, $C_1$-$C_6$ alkoxy, and $NO_2$. In one embodiment, $R_1$, $R_2$, $R_4$, $R_5$, $R_6$, $R_8$, $R_{10}$, $R_{11}$, and $R_{13}$ of Formula 1 are all H and the remaining R groups are as defined above. In another embodiment, $R_1$, $R_2$, $R_4$, $R_5$, $R_6$, $R_8$, $R_{10}$, $R_{11}$, and $R_{13}$ of Formula 1 are all H, $R_3$ is selected from H, $CH_3$, $OCH_3$, and $NO_2$, $R_7$ and $R_9$ are each independently selected from H and $OCH_3$, and $R_{12}$ and $R_{14}$ are each independently selected from H, Br, I, and $NO_2$. In another embodiment, $R_1$, $R_2$, $R_4$, $R_5$, $R_6$, $R_8$, $R_{10}$, $R_{11}$ and $R_{13}$ of Formula 1 are all H, $R_3$ is selected from H, $CH_3$, OH, $OCH_3$ and $NO_2$, $R_7$ and $R_9$ are each independently selected from H and $OCH_3$, $R_{12}$ is selected from H, Br, I and $NO_2$, and $R_{14}$ is selected from H, OH, Cl, Br, I and $NO_2$.

In certain specific embodiments, $R_1$, $R_2$, $R_4$, $R_5$, $R_6$, $R_8$, $R_{10}$, $R_{11}$, and $R_{13}$ of Formula 1 are all H, and a) $R_3$ is $CH_3$ and $R_7$, $R_9$, $R_{12}$, and $R_{14}$ are all H (Compound 1), b) $R_3$, $R_7$, $R_9$, $R_{12}$, and $R_{14}$ are all H (Compound 2), c) $R_3$ is $CH_3$, $R_{14}$ is Cl, and $R_7$, $R_9$, and $R_{12}$ are all H (Compound 3), d) $R_3$ is $CH_3$, $R_{14}$ is OH and $R_7$, $R_9$, and $R_{12}$ are all H (Compound 4), e) $R_{14}$ is OH and $R_3$, $R_7$, $R_9$, and $R_{12}$ are all H (Compound 5), f) $R_3$ is OH and $R_7$, $R_9$, $R_{12}$, and $R_{14}$ are all H (Compound 6), g) $R_{14}$ is $NO_2$ and $R_3$, $R_7$, $R_9$, and $R_{12}$ are all H (Compound 7), h) $R_{12}$ is Br, $R_{14}$ is $NO_2$ and $R_3$, $R_7$, and $R_9$ are all H (Compound 8), i) $R_3$ and $R_9$ are both $OCH_3$, $R_{12}$ is Br, $R_{14}$ is $NO_2$ and $R_7$ is H (Compound 9), or j) $R_3$ and $R_9$ are both $OCH_3$, $R_{14}$ is $NO_2$ and $R_7$ and $R_{12}$ are both H (Compound 10).

The term "$^{85}Rb_e$" is used herein to refer to rubidium that is enriched for $^{85}$Rb, also referred to as "$^{85}$Rb-enriched rubidium." Compound 1 above is also referred to herein as the $^{85}$Rb-enriched rubidium organic salt of N-benzoyl-N'-(4-toluenesulfonyl)-o-phenylenediamine and as "E2+$^{85}Rb_e$" and "$^{85}Rb_e$-E2." "E2" refers to N-benzoyl-N'-(4-toluenesulfonyl)-o-phenylenediamine.

In any of the above compounds, the rubidium preferably is at least 75% $^{85}$Rb, more preferably at least 85% $^{85}$Rb, and still more preferably at least 95% $^{85}$Rb, and in some embodiments is at least 99% $^{85}$Rb, such as 99.8% $^{85}$Rb. "Rb that is N % $^{85}$Rb" refers to Rb of which N % of the Rb atoms are the isotope $^{85}$Rb.

It is another object of the invention to provide the compound of Formula 2:

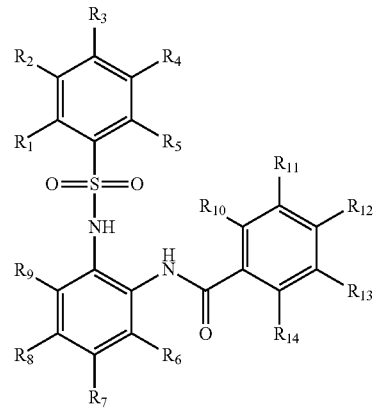

Formula 2 and salts thereof. Exemplary salts include the sodium salt, potassium salt, and rubidium salt.

In the compound of Formula 2, each of $R_1$ through $R_{14}$ is independently selected from H, OH, F, Cl, Br, I, $C_1$-$C_6$ alkyl, $C_1$-$C_6$ alkoxy, and $NO_2$. In one embodiment, $R_1$, $R_2$, $R_4$, $R_5$, $R_6$, $R_8$, $R_{10}$, $R_{11}$, and $R_{13}$ of Formula 2 are all H and the remaining R groups are as defined above. In another embodiment, $R_1$, $R_2$, $R_4$, $R_5$, $R_6$, $R_8$, $R_{10}$, $R_{11}$, and $R_{13}$ of Formula 2 are all H, $R_3$ is selected from H, $CH_3$, $OCH_3$, and $NO_2$, $R_7$ and $R_9$ are each independently selected from H and $OCH_3$, and $R_{12}$ and $R_{14}$ are each independently selected from H, Br, I, and $NO_2$. In certain specific embodiments, $R_1$, $R_2$, $R_4$, $R_5$, $R_6$, $R_8$, $R_{10}$, $R_{11}$, and $R_{13}$ of Formula 2 are all H, and a) $R_3$ is $CH_3$ and $R_7$, $R_9$, $R_{12}$, and $R_{14}$ are all H (Compound 11), b) $R_3$, $R_7$, $R_9$, $R_{12}$, and $R_{14}$ are all H (Compound 12), c) $R_3$ is $CH_3$, $R_{14}$ is Cl, and $R_7$, $R_9$, and $R_{12}$ are all H (Compound 13), d) $R_3$ is $CH_3$, $R_{14}$ is OH and $R_7$, $R_9$, and $R_{12}$ are all H (Compound 14), e) $R_{14}$ is OH and $R_3$, $R_7$, $R_9$, and $R_{12}$ are all H (Compound 15), f) $R_3$ is OH and $R_7$, $R_9$, $R_{12}$, and $R_{14}$ are all H (Compound 16), g) $R_{14}$ is $NO_2$ and $R_3$, $R_7$, $R_9$, and $R_{12}$ are all H (Compound 17), h) $R_{12}$ is Br, $R_{14}$ is $NO_2$ and $R_3$, $R_7$, and $R_9$ are all H (Compound 18), i) $R_3$ and $R_9$ are both $OCH_3$, $R_{12}$ is Br, $R_{14}$ is $NO_2$ and $R_7$ is H (Compound 19), or j) $R_3$ and $R_9$ are both $OCH_3$, $R_{14}$ is $NO_2$ and $R_7$ and $R_{12}$ are both H (Compound 20).

Compound 11 above is also referred to herein as N-benzoyl-N'-(4-toluenesulfonyl)-o-phenylenediamine and as "E2".

In another aspect, the invention provides methods of synthesizing the compounds of formula 1 and the compounds of formula 2, as diagrammed below.

Phase 1. Aryl sulfonation

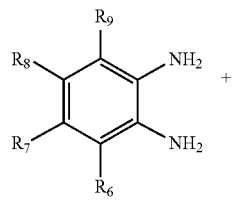

(i)

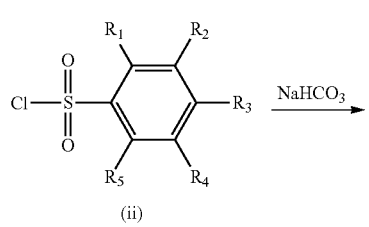

(ii)

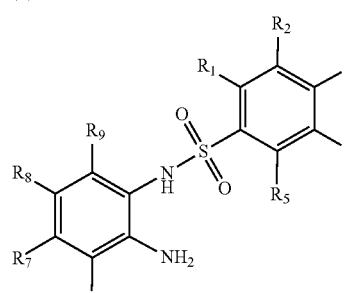

(iii)

Phase 2. Acylation

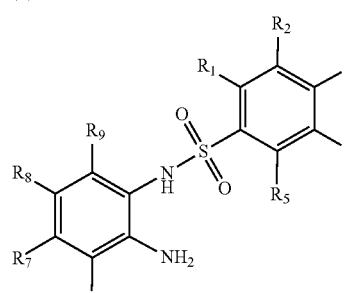

(iii)

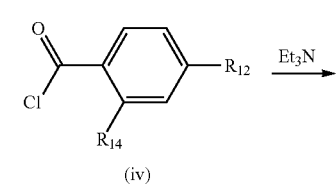

(iv)

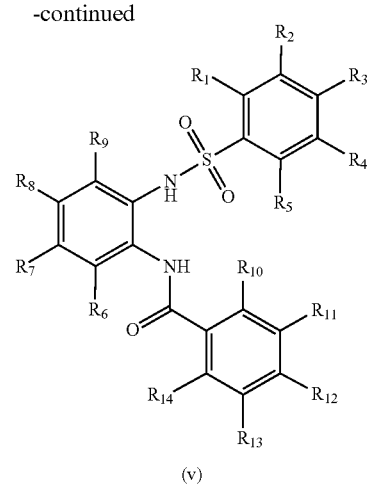

(v)

Phase 3. Obtaining rubidium complex. To prepare $^{85}Rb$-enriched compounds, $^{85}Rb_eCl$ ($^{85}Rb_e$ is 99% $^{85}Rb$, for example) is used in the final step shown below.

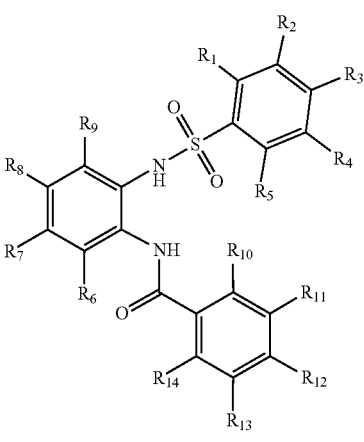

(v)

+ KOH ⟶

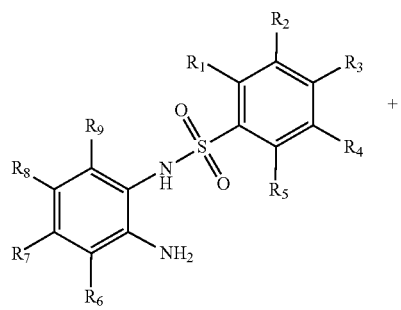

+ RbCl ⟶

(vi)

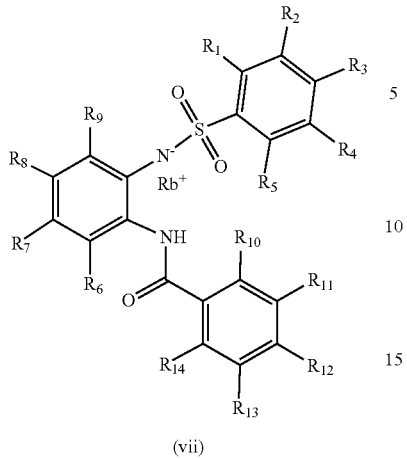

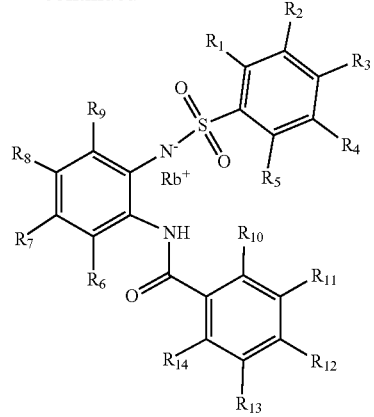

(vii)

In another aspect, the invention provides a method of synthesizing a compound of formula 1 that uses a compound of formula 2 or a salt thereof as starting material or as an intermediate in the synthesis of the compound of formula 1. In an embodiment, the R groups of the compound of formula 2 and salts thereof are the same as the corresponding R groups of the compound of formula 1. In an embodiment, the synthetic method proceeds as outlined below:

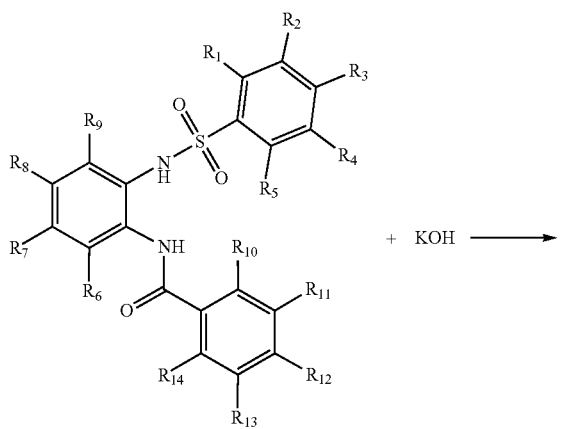

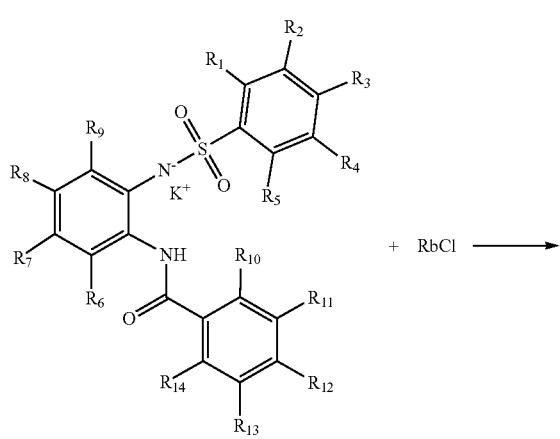

This synthesis produces the potassium salt as an intermediate and the rubidium salt as the product. In an analogous method, $^{85}Rb_eCl$ can be used instead of RbCl to obtain a product in which the rubidium is enriched for $^{85}Rb$.

In another aspect, the invention provides compositions that comprise one or more compounds of general formula 1, above, or one or more compounds of a sub-genus thereof as described above, or one or more of the above-recited $^{85}Rb$-enriched compounds 1-10. The invention also provides compositions that comprise a compound of general formula 2, above, or a compound of a sub-genus thereof as described above, or one or more of the above-recited compounds 11-20. The compositions include any type known in the art, including but not limited to liquid compositions formulated for intravenous or other parenteral administration, compositions formulated for topical administration, and compositions formulated for oral administration, such as, for example, tablets, pills, capsules, lozenges, granules. In certain embodiments, the compositions of the invention comprise between 0.4 millimoles and 30 millimoles of a compound of the invention, such as between 1 millimole and 10 millimoles, or such as 1, 2, 5, 10, 20, 25, or 30 millimoles. The compositions of the invention further comprise one or more excipients appropriate to the formulation. Intravenous formulations of the invention comprise at least one of: an appropriate solvent, such as water; a salt or ions such as sodium chloride, potassium chloride, potassium ion, sodium ion, chloride ion; a sugar such as glucose and sucrose; a buffer; other conventional excipients, such as DMSO. Topical formulations of the invention include but are not limited to ointments, creams, lotions, salves and comprise at least one of: an appropriate vehicle; a penetration enhancer, such as DMSO and related analogues; and an emulsifier. Tablets of the invention comprise at least one conventional excipient such as, for example: a filler (e.g. starches, lactose, sucrose, glucose); a binder (e.g. carboxymethylcellulose, gelatin, polyvinylpyrrolidone, sucrose); a disintegrating agent (e.g. calcium carbonate, alginic acid, sodium carbonate); a wetting agent (e.g. cetyl alcohol, and glycerol monostearate, sodium lauryl sulfate); a buffering agent; a lubricant (e.g. talc, calcium stearate, magnesium stearate, solid polyethylene glycols, sodium lauryl sulfate); and a coating.

In another aspect, the invention provides a method of treating a condition that comprises administering a compound of the invention or a composition of the invention, as set forth above. In an embodiment, the condition treated is cancer, such as melanoma. In an embodiment, the method of the invention is a method of treating cancer or suppressing cancer growth that comprises administering the $^{85}$Rb-enriched rubidium compound of Formula 1 or composition that comprises it either alone or in combination with a conventional form of cancer therapy, such as chemotherapy (e.g. antitumor drugs, such as antitumor drugs currently known and used in cancer therapy) or with other known cancer therapies such as radiation treatment. In various embodiments, the compound or composition of the invention is administered before, simultaneously with, or after the chemotherapy or other known anticancer therapy is administered. When not administered simultaneously, the interval between administrations is about 48 hours or less, such as 36 hours or less, or 24 hours or less.

In another aspect, the invention provides a composition for use in the treatment of a condition, in a human or in a veterinary animal, such as a dog, cat, cow or horse, wherein the composition is any of the compositions described above. In an embodiment, the condition treated is cancer, such as melanoma. In various embodiments, the composition comprises one or more than one of the $^{85}$Rb-enriched rubidium compounds described above, such as the $^{85}$Rb-enriched rubidium compound of Formula 1. In an embodiment, the composition further comprises another suitable active ingredient, such as an antitumor drug, such as an antitumor drug currently known and used in cancer therapy.

In another aspect, the invention provides a composition for use in the suppression of cancer growth, wherein the composition is any of the compositions described above. In an embodiment, the cancer growth suppressed is melanoma. In various embodiments, the composition comprises one or more than one of the $^{85}$Rb-enriched rubidium compounds described above, such as the $^{85}$Rb-enriched rubidium compound of Formula 1. In an embodiment, the composition further comprises another suitable active ingredient, such as an antitumor drug, such as an antitumor drug currently known and used in cancer therapy.

In another aspect, the invention provides a compound for use in the treatment of a condition, in a human or in a veterinary animal, such as a dog, cat, cow or horse, wherein the compound is any of the $^{85}$Rb-enriched rubidium compounds of Formula 1 described above. In an embodiment, the condition treated is cancer, such as melanoma.

In another aspect, the invention provides a compound for use in the suppression of cancer growth, wherein the compound is any of the $^{85}$Rb-enriched rubidium compounds of Formula 1 described above. In an embodiment, the cancer growth suppressed is melanoma.

Figure 1:
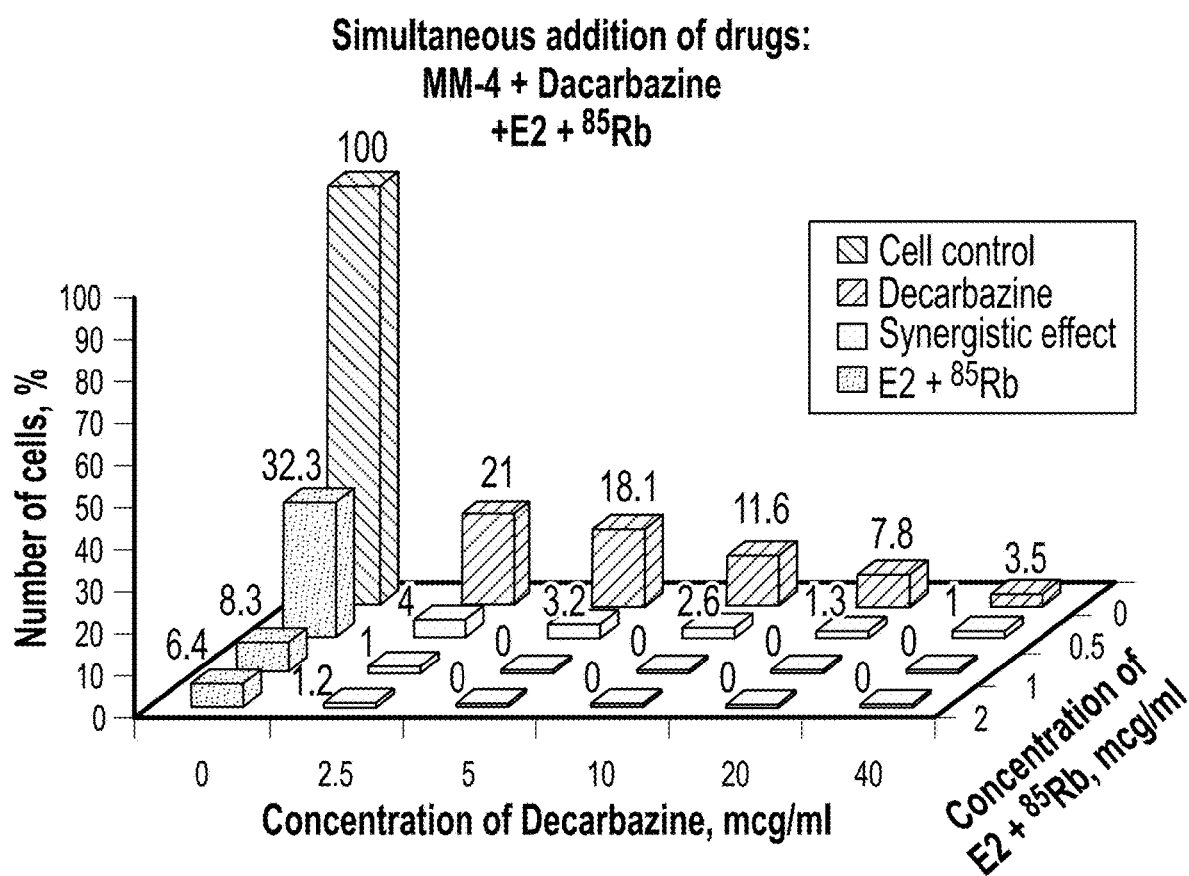
FIG. 1 shows the efficacy data (synergistic effect) in mouse B16 melanoma cells (MM-4 cell line) for a composition that comprises the $^{85}$Rb-enriched rubidium salt of N-benzoyl-N'-(4-toluenesulfonyl)-o-phenylenediamine and the antitumor drug dacarbazine (Example 2).
Figure 2:
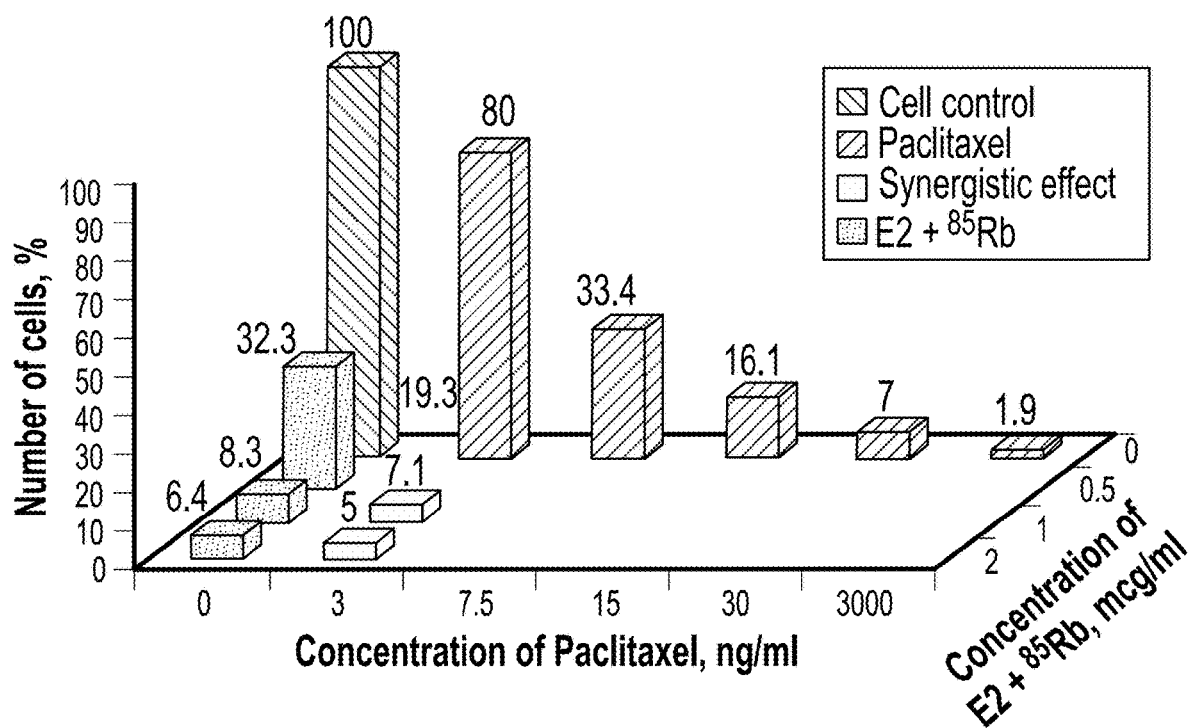
FIG. 2 shows the efficacy data in mouse melanoma cells (MM-4 cell line) for a composition that comprises the $^{85}$Rb-enriched rubidium salt of N-benzoyl-N'-(4-toluenesulfonyl)-o-phenylenediamine and the antitumor drug paclitaxel (antagonistic interaction was observed) (Example 2).
Figure 3:
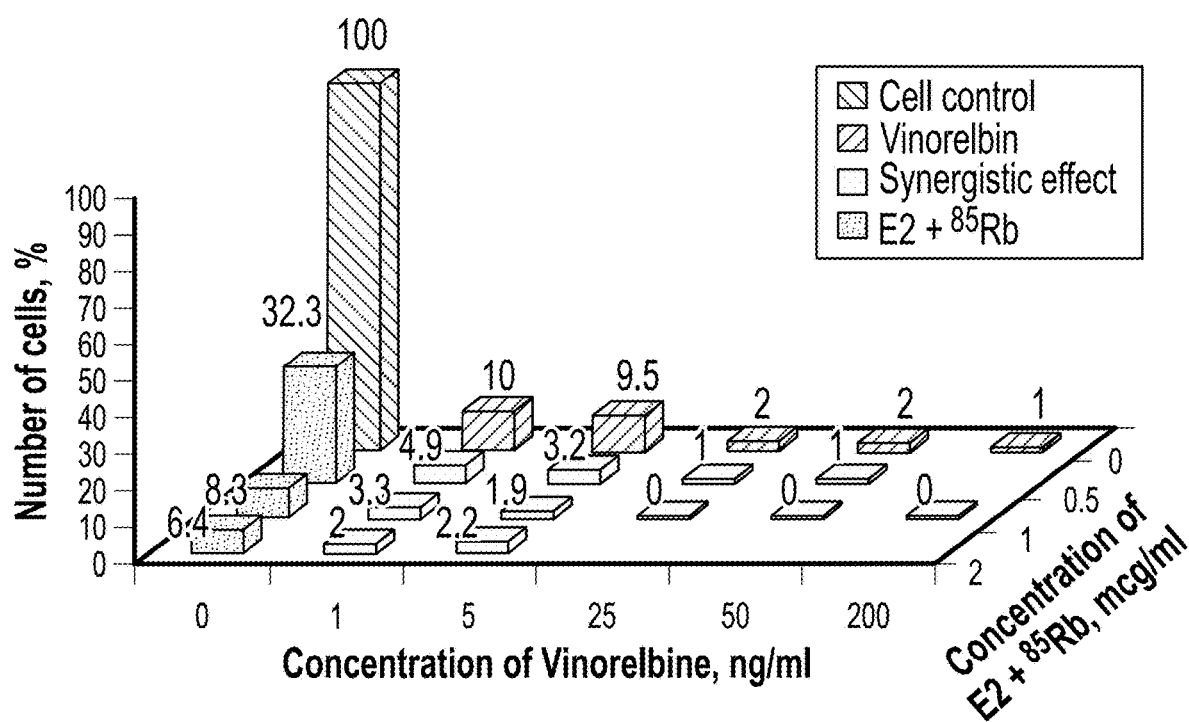
FIG. 3 shows the efficacy data (synergistic effect) in mouse melanoma cells (MM-4 cell line) for a composition that comprises the $^{85}$Rb-enriched rubidium salt of N-benzoyl-N'-(4-toluenesulfonyl)-o-phenylenediamine and the antitumor drug vinorelbine (Example 2).

(In the Figures, in numbers that contain commas, the comma indicates a decimal point-for example, "4,5" indicates "4.5" and "1,5" indicates "1.5".)

DETAILED DESCRIPTION OF THE INVENTION

The present invention relates to a method, compound and composition for the suppression, in humans and in veterinary animals, of cancer growth, melanoma in particular. The present invention makes it possible to eliminate shortcomings of the prior art technical solutions. The compounds of the invention include $^{85}$Rb-enriched rubidium ("$^{85}$Rb$_e$") salts (also referred to as a rubidium complex or compound) of general Formula 1:

Formula 1

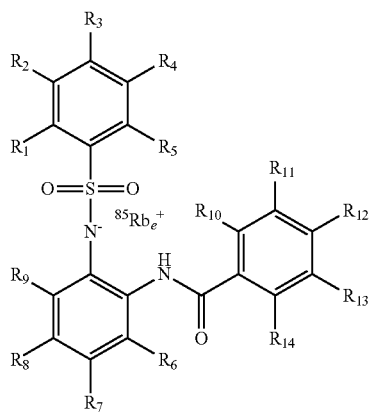

wherein each of R$_1$ through R$_{10}$ is independently selected from H, OH, F, Cl, Br, I, C$_1$-C$_6$ alkyl, C$_1$-C$_6$ alkoxy, and NO$_2$.

In an exemplary embodiment, Compound 1 of the invention, R$_3$ is CH$_3$ and the remaining R groups are H. This compound is also referred to herein as the $^{85}$Rb-enriched rubidium organic salt of N-benzoyl-N-(4-toluenesulfonyl)-o-phenylenediamine and as "$^{85}$Rb$_e$–E2" and "E2+$^{85}$Rb$_e$." "E2" refers to N-benzoyl-N'-(4-toluenesulfonyl)-o-phenylenediamine. (In the Figures, the terms "E2+$^{85}$Rb", "E2Rb85", and "85RbE2" refer to $^{85}$Rb$_e$–E2.) Compounds of the present invention are prepared as disclosed herein and using chemical synthetic methods disclosed in the literature.

Rubidium is a chemical element of the main subgroup of group 1, period 5, of the periodic table, with atomic number 37. $^{85}$Rb is a stable isotope which has a percent natural abundance of 72.2%. That is, naturally occurring rubidium consists of a mixture of rubidium isotopes. In a sample of naturally occurring rubidium, 72.2% of the rubidium atoms are isotope $^{85}$Rb. As used herein, "$^{85}$Rb-enriched rubidium" is rubidium that consists of more than 72.2% $^{85}$Rb. Thus, in compounds of the present invention, the rubidium is more than 72.2% $^{85}$Rb, such as at least about 75% (e.g. at least 75%), at least about 80% (e.g. at least 80%), at least about 85% (e.g. at least 85%), at least about 90% (e.g. at least 90%), or at least about 95% $^{85}$Rb (e.g. at least 95% $^{85}$Rb). In preferred embodiments of the compound, composition, and methods of the present invention, the rubidium is at least about 90% $^{85}$Rb (e.g. at least 90% $^{85}$Rb) and may be over 99% $^{85}$Rb, such as about 99.8% $^{85}$Rb (e.g. 99.8% $^{85}$Rb). The compositions of the present invention comprise such $^{85}$Rb-enriched compounds, and the methods of the invention entail administering such compositions. The term "about" as used herein indicates plus or minus 3% of the subject amount (e.g., "about 80%" refers to the range from 77.6% to 82.4%).

A compound of Formula 1 is effective in suppressing cancer growth. In vitro, a compound of Formula 1 is used at a concentration of from about 0.5 µg/ml to about 2 µg/ml of tissue culture medium and the antitumor drug is used at a dose of 1 ng/ml-40 µg/ml. The compound is administered in vivo at a dose between about 0.05 mg of $^{85}$Rb$_e$/kg and about 100 mg of $^{85}$Rb$_e$/kg, preferably between about 1 mg of $^{85}$Rb$_e$/kg and about 20 mg of $^{85}$Rb$_e$/kg, and more preferably between 1.25 and 12.5 mg $^{85}$Rb$_e$ per kg body mass. In some embodiments, the $^{85}$Rb$_e$ compounds of the invention are used in vivo at a dose of about 5 mg of $^{85}$Rb$_e$/kg, about 10 mg of $^{85}$Rb$_e$/kg, or about 15 mg of $^{85}$Rb$_e$/kg. In certain embodiments, these dosages are the amount administered daily. For example, where the $^{85}$Rb$_e$ compound is to be administered at a dose of 10 mg of $^{85}$Rb$_e$/kg to a subject having a mass of 70 kg, the appropriate composition would comprise 700 mg of $^{85}$Rb$_e$ provided in the form of the $^{85}$Rb$_e$ salt. Where the composition is a liquid to be infused or injected, for example, the total amount of $^{85}$Rb$_e$ infused or injected in the form of the $^{85}$Rb$_e$ salt would be 700 mg. As indicated, the above doses are the dose of the $^{85}$Rb$_e$. The molar equivalent of the corresponding salt compound of the invention would be greater in mass. For a dosage range of between 1 mg of $^{85}$Rb$_e$/kg and 20 mg of $^{85}$Rb$_e$/kg and a body weight range of 40 kg to 120 kg, a composition of the invention contains a compound of Formula 1 in an amount equivalent to between 40 mg $^{85}$Rb$_e$ and 2400 mg $^{85}$Rb$_e$. For a dosage range of between 1.25 mg of $^{85}$Rb$_e$/kg and 12.5 mg of $^{85}$Rb$_e$/kg and a body weight range of 40 kg to 120 kg, a composition of the invention contains a compound of Formula 1 in an amount equivalent to between 50 mg $^{85}$Rb$_e$ and 1500 mg $^{85}$Rb$_e$. In certain embodiments, the dosage can be subdivided for administration more than once daily, and the composition can contain the corresponding fraction of the total daily dose, e.g. ½ the daily dose for twice daily administration, ⅓ the daily dose for thrice daily administration.

A composition of the present invention comprises one or more compounds of Formula 1, such as any of Compounds 1-10 (e.g. the $^{85}$Rb-enriched rubidium salt of N-benzoyl-N'-(4-toluenesulfonyl)-o-phenylenediamine), and optionally also contains one or more conventional antitumor drugs, for example, one or more antitumor drugs selected from the group that includes dacarbazine, doxorubicin, paclitaxel, vinorelbine and cisplatin, and also optionally contains one or more adjuvant agents. In an embodiment of the invention, the composition contains a compound of Formula I, such as Compound 1, and an antitumor drug selected from dacarbazine and vinorelbine. In a composition of the invention that contains both the $^{85}$Rb-enriched rubidium salt of formula I and the antitumor drug, the $^{85}$Rb$_e$ salt is present at the in vivo doses set forth above, and the antitumor drug is present at a dose that is between 0.05 and 2.5 times the approved dosage (that is, at the dosage that the antitumor drug would have been prescribed if not administered in conjunction with a compound of the invention).

Compositions of the present invention otherwise are those conventional forms known in the art for administration to humans or animals. The compositions of the present invention are prepared using methods within the general practice applied in the pharmaceutical industry, such as, for example, methods illustrated in the latest edition of Remington's Pharmaceutical Science Handbook, Mack Pub. N.Y., USA. Compositions of the invention comprise at least one pharmaceutically acceptable vehicle or excipient. These include, in particular, for example, diluents, fillers, disintegrants, solubilizing agents, dispersing agents, preservatives, wetting agents, preservatives, stabilizers, buffering agents (e.g. phosphate, citrate, acetate, tartrate), suspending agents, emulsifiers, and penetration enhancing agents such as DMSO, as appropriate. Compositions of the invention preferably are solutions for injection, such as intravenous injection. Water is preferably used as a dosing vehicle and diluent in an injectable composition. Other pharmaceutically acceptable solvents and diluents may also be used in addition to or instead of water, such as saline, glycerol and ethanol. A complete description of pharmaceutically acceptable excipients can be found, for example, in *Remington's Pharmaceutical Sciences* (Mack Pub., Co., N.J. 1991) or other standard pharmaceutical science texts, such as the *Handbook of Pharmaceutical Excipients* (Shesky et al. eds., 8th ed. 2017).

Large macromolecules that are slowly metabolized, such as proteins, polysaccharides, polylactic acids, polyglycolic acids, polymeric amino acids, and copolymers of amino acids can also be used as vehicles for the agent and composition.

In addition, compositions of the invention may be as described above, but comprise a compound of Formula 2, or a salt thereof, such as a sodium, potassium, or rubidium salt (not enriched for $^{85}$Rb) instead of, or in addition to, a compound of Formula 1.

The invention provides a method that comprises administering to a human or to a veterinary animal a compound or composition of the invention and optionally at least one conventional form of cancer therapy, such as anti-cancer radiation therapy or one or more antitumor drugs (abbreviated herein "AD"). The method may be used to treat cancer and/or suppress cancer growth, such as melanoma. High efficiency of the method is achieved when a compound of the invention, such as the $^{85}$Rb-enriched rubidium salt of N-benzoyl-N-(4-toluenesulfonyl)-o-phenylenediamine (Compound 1), is administered in vivo at a dose as described above first, and then, after an interval of time, an antitumor drug is administered. In an embodiment, the antitumor drug is selected from the group that includes dacarbazine, doxorubicin, paclitaxel, vinorelbine and cisplatin. In preferred embodiments, the antitumor drug is administered at its approved dosage (that is, at the dosage at which the antitumor drug would have been prescribed in the absence of a compound of the invention). In other embodiments, the antitumor drug is administered at some fraction of its approved dosage, such as one-tenth, one-fifth, one-fourth, one-third, or one-half the approved dosage. For example, where the antitumor drug is cisplatin, 1.5 mg/kg of cisplatin would be administered three times at 48-hour intervals to provide the approved dosage of cisplatin. The time between administration of the $^{85}$Rb$_e$ salt and administration of the antitumor drug is preferably between about 12 and about 24 hours. In some embodiments, the interval is between about 6 and about 36 hours, or between about 3 and about 48 hours. Exemplary intervals include 12, 18, 24, 30, and 36 hours. In alternative embodiments, a compound of the invention is administered at the same time as an AD or after the AD at an interval as described above.

The antitumor drugs (ADs) referred to above include, but are not limited to, nitrosoureas (e.g., carmustine (BCNU) and lomustine (CCNU)), alkylsulphonates (e.g., busulfan and treosulfan), triazenes (e.g., dacarbazine, temozolomid), platinum-based compounds (e.g., cisplatin, carboplatin, oxaliplatin), vinca alkaloids (e.g., vincristine, vinblastine, vindesine and vinorelbine), taxoids (e.g., paclitaxel or paclitaxel equivalents or paclitaxel analogs (such as docetaxel), anti-metabolites, DHFR inhibitors (e.g., methotrexatum, dichloromethotrexate, trimetrexate, edatrexate), and anthracyclines (e.g., daunorubicin, doxorubicin, pegylated liposomal doxorubicin, idarubicin, epirubicin, mitoxantrone). While an expected range of AD dosage is between about 1 ng/ml and 50 µg/ml, the AD drug's dosage typically will be determined based on its known dosage when used without the rubidium salt of the invention.

An advantage of the present invention is that the combination of the $^{85}$Rb-enriched rubidium salt of the invention and an antitumor drug provide a synergistic effect. As a consequence, less of the antitumor drug can be used when used in combination with rubidium salt of the invention than when the antitumor drug is used alone. The side effects associated with use of the antitumor drug therefore can be diminished when used in combination with the rubidium salt of the invention.

An $^{85}$Rb-enriched rubidium salt of N-benzoyl-N'-(4-toluenesulfonyl)-o-phenylenediamine (Compound 1) was synthesized by the present inventors. The enriched rubidium was 99.8% $^{85}$Rb. The inventors have surprisingly found that the said compound is effective in suppressing cancer growth. The inventors of the present invention have developed and investigated the possibility and effectiveness of using the said compound in combination with antitumor drugs when administered sequentially. They have further discovered that an additive and even synergistic effect on the suppression of cancer growth may be achieved by administering the $^{85}$Rb-enriched rubidium salt of N-benzoyl-N'-(4-toluenesulfonyl)-o-phenylenediamine of formula I following the preliminary administration of one or more antitumor drugs ("ADs").

For any compound, a therapeutically effective dose can be estimated initially from cell culture or animal model assays. Mice, rats, guinea pigs, rabbits, dogs or pigs are commonly used as models in animal testing. An animal model can be used to determine the appropriate range of concentrations and route of administration. Such information can then be used to determine appropriate doses and routes of administration in humans. To estimate human equivalent dose, it is recommended to use the dosage conversion table given in the Guidance for Industry and the Reviewers document (2002, U.S. Food and Drug Administration, Rockville, MD, USA). The exact effective dose to a patient will depend on various considerations, including the severity of illness, the overall health of the patient, age, body weight and sex of the patient, nutrition, time and frequency of administration, route of administration, combination(s) of medicaments, reaction sensitivity and tolerability/response to therapy. The exact dose can be determined by routine experiments and according to the attending physician's professional judgment and discretion.

The agent and $^{85}$Rb$_e$-compound-containing composition of the present invention are preferably administered intravenously or intramuscularly. Other conventional routes of administration may also be used, including other routes of injection and via oral and topical administration.

In an embodiment of the invention, one or more of dacarbazine, paclitaxel and vinorelbine are used as antitumor drugs included in the composition. The total dose of a compound of Formula 1 of the invention is between about 1.25 mg $^{85}$Rb$_e$/kg body weight and about 12.5 mg $^{85}$Rb$_e$/kg body weight, and the total dose of any of these three antitumor drugs is between about 0.45 mg/kg body weight and about 4.5 mg/kg body weight.

In an embodiment of the invention, the composition of the invention (preferably containing a compound of Formula 1, such as any of compounds 1-10) is used to treat melanoma as a form of cancer. In another embodiment, a method of treating melanoma is provided that comprises the sequential administration of one or more antitumor drugs either before or after the administration of the composition of the invention. The interval between administration of one or more ADs and the administration of the composition of the invention is between about 12 hours and about 30 hours, preferably between about 20 hours and 28 hours, more preferably about 24 hours, such as 24 hours.

Melanoma (or skin cancer) is a common type of cancer that occurs in patients of any age. The disease typically starts in either the pigment-producing cells of the skin called melanocytes, which make melanin, or from pigmented tissues, such as moles (also known as pigmented nevi). This form of cancer is characterized by rapid development. Along with squamous cell carcinoma and basal cell carcinoma, melanoma is referred to as a malignant skin tumor. Most frequently it originates in the skin, less often in the retina of the eye and rarely in the mucous membranes of the oral cavity, genitalia or rectum. Melanoma is one of the most dangerous types of all human cancers, often recurring and spreading both hematogenously and through lymphatic vessels to almost all organs in the body. A peculiar feature of this form of cancer is a weak immune response of an organism to the tumor, or even absence thereof, which is why very often melanoma progresses rapidly. This type of pathology accounts for 10 percent of all malignant skin lesions. It takes third place in frequency among all cancers in people belonging to the 15 to 39 age group.

The present inventors have surprisingly found that the compound of Formula 1, such as the $^{85}$Rb-enriched rubidium salt of N-benzoyl-N'-(4-toluenesulfonyl)-o-phenylenediamine (Compound 1), in combination with an antitumor drug (AD), suppresses cancer growth. In particular, the compound of Formula 1, the agent based thereon and the composition increase survival in in vitro and in vivo studies in model systems.

An advantage of a compound of Formula 1 and a composition comprising it as described above is that their use enables reduction of toxic effects which are common to most methods based on the use of known cytostatic agents, while improving their efficacy in eradicating the established tumor. Due to the important physiological role of rubidium used in the composition and the method of producing the novel compound so that it is enriched for $^{85}$Rb, in addition to antitumor effect, it is possible to gain a number of additional advantages associated with the optimization of the catalytic, structural and regulatory function of the organism.

High antitumor activity of a compound of Formula 1, in combination with an AD, in particular, high cytotoxic and cytostatic effects on melanoma cells, was demonstrated in in vitro experiments on cell culture and in vivo experiments in mice, wherein an additive and even synergistic effect was achieved. Such synergy enables the use of lower doses of chemotherapeutic agents thereby reducing their toxic effects on healthy cells, as is common to most methods based on the use of known cytostatic agents, while improving their efficacy in eradicating the established tumor. Due to the important physiological role of rubidium used in the composition and the method of producing the novel compound, in addition to antitumor effect, it is possible to gain a number of additional advantages associated with the optimization of the catalytic, structural and regulatory function of the organism.

It is especially important that the cytotoxic effect of AD on normal cells is reduced with a combined administration of AD and an $^{85}$Rb$_e$ salt compound of the invention. A relatively high antitumor activity of the methods of the invention, in particular, the ability to provide high cytotoxic and cytostatic effects on melanoma cells, was demonstrated in in vitro experiments on cell culture and in vivo experiments in mice.

The present invention is described more fully hereinafter by reference to the following examples, which are presented by way of illustration only and should not be construed in any way to limit the scope of the present invention.

A synthetic scheme for preparing certain compounds of the invention and for use according to the invention is set forth below.

Phase 1. Aryl sulfonation of o-phenylenediamine:

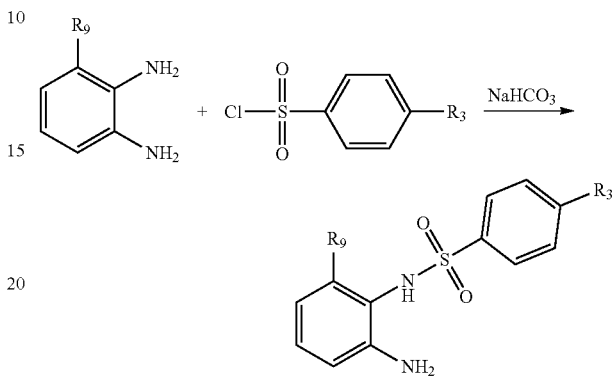

Phase 2. Acylation of N-R$_3$-phenylsulfonyl-o-phenylenediamine:

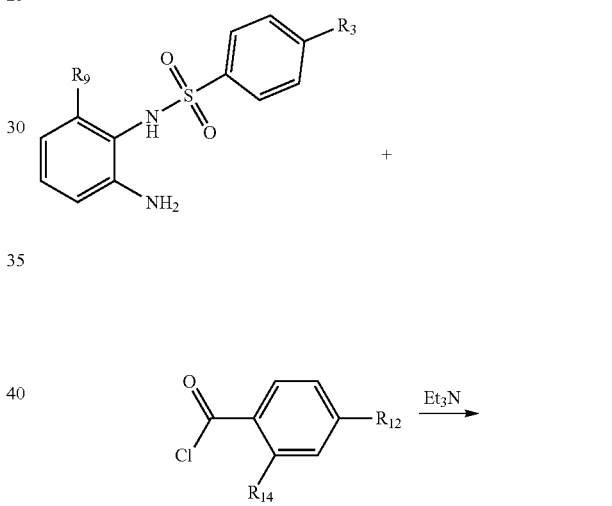

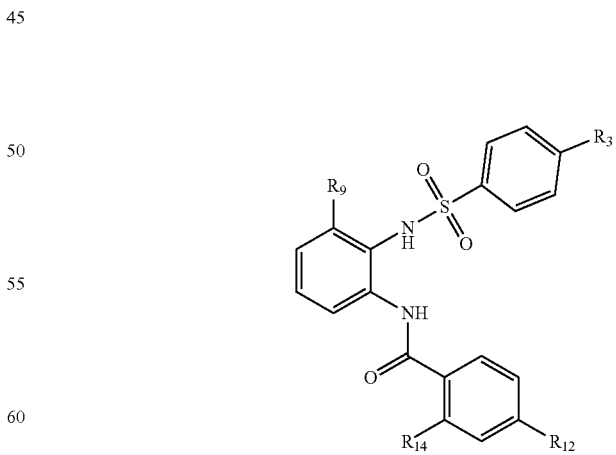

Phase 3. Obtaining of N—(R12, R14-benzoyl)-N'—(R3-phenylsulfonyl)-o-phenylenediamine rubidium complex. To prepare $^{85}$Rb-enriched compounds, $^{85}$Rb$_e$Cl ($^{85}$Rb$_e$ is 99% $^{85}$Rb, for example) is used in the final step shown below.

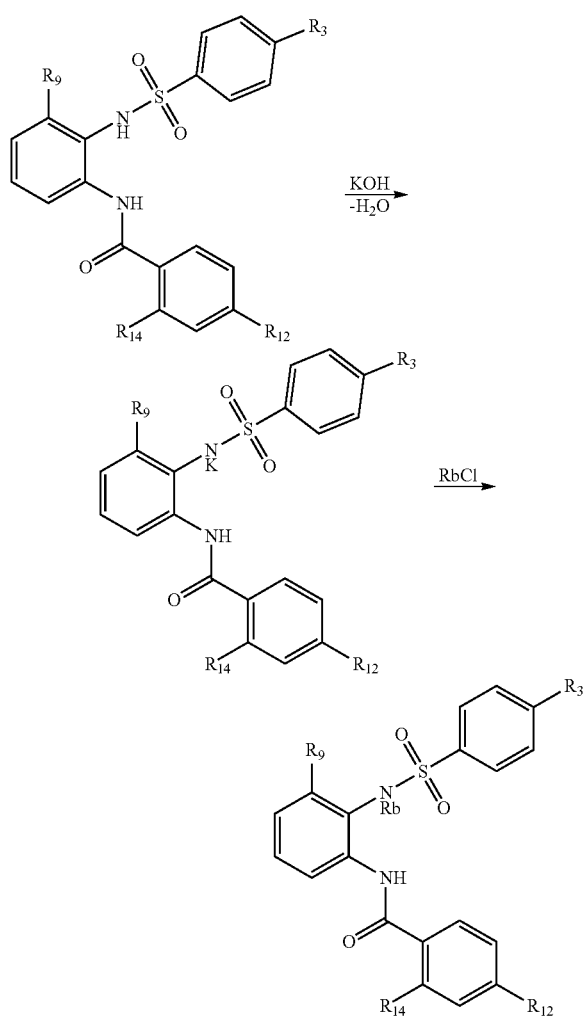

Compounds 1-10 were prepared by the above synthesis.

EXAMPLES

Example 1. In Vitro Study of the Cytotoxic Activity of the Compound Comprising the $^{85}$Rb-Enriched Rubidium Salt of N-benzoyl-N'-(4-toluenesulfonyl)-o-Phenylenediamine of Formula I According to the Invention in B16 Melanoma Cells In vitro effects of experimental compound $^{85}$Rb$_e$–E2 on metabolic activity of human keratinocytes (HaCaT line)

| Concentration of compounds | E2 + Rb reference drug | $^{85}$Rb$_e$ – E2 |
|---|---|---|
| | Metabolic activity of cells, % * | |
| 1 µg/ml | 130 ± 2 | 0 |
| 0.5 µg/ml | 103 ± 2.7 | 90 ± 1 |
| 0.25 µg/ml | 95 ± 1.7 | 100 ± 8.7 |
| 0.13 µg/ml | 87.5 ± 6.7 | 95.3 ± 10.7 |
| 62 ng/ml | 97.3 ± 4.1 | 90.7 ± 2.7 |
| 31 ng/ml | 99.2 ± 12.5 | 97.8 ± 3.6 |
| 16 ng/ml | 104.7 ± 3.2 | 98 ± 4 |
| 8 ng/ml | — | 114 ± 7.7 |

In vitro assessment of the effects of experimental compound $^{85}$Rb$_e$–E2 on metabolic activity of normal human fibroblasts (MTT assay)

| Concentration of compounds | E2 + Rb reference drug | $^{85}$Rb$_e$ – E2 |
|---|---|---|
| | Metabolic activity of cells, % * | |
| 150 µg/ml | 99.3 ± 3.2 | 72.8 ± 2.1 |
| 75 µg/ml | 97.7 ± 7.5 | 67.4 ± 4.7 |
| 38 µg/ml | 98.8 ± 7.1 | 68.5 ± 1.8 |
| 20 µg/ml | 96.8 ± 9.8 | 74 ± 1.3 |
| 10 µg/ml | 104.6 ± 14.2 | 82.5 ± 1.3 |
| 5 µg/ml | 103.4 ± 9.3 | 82.3 ± 3 |
| 2.5 µg/ml | 128.2 ± 8.3 | 84.4 ± 4.6 |
| 1.25 µg/ml | — | 105.1 ± 2.3 |

In vitro assessment of cytotoxic/cytostatic effects of experimental compound $^{85}$Rb$_e$–E2 on mouse bone marrow cells (MTT assay)

| Concentration of compounds | E2 + Rb reference drug | $^{85}$Rb$_e$ – E2 |
|---|---|---|
| | Metabolic activity of cells, % * | |
| 150 µg/ml | 107.1 ± 3.8 | 0 |
| 75 µg/ml | 105.2 ± 7.8 | 18.5 ± 0.4 |
| 38 µg/ml | 96.2 ± 4.4 | 19.1 ± 1.9 |
| 20 µg/ml | 88 ± 3.5 | 24.2 ± 0.8 |
| 10 µg/ml | 99.3 ± 4.7 | 45 ± 4.7 |
| 5 µg/ml | 106.7 ± 11.8 | 90.2 ± 3.3 |
| 2.5 µg/ml | 106.8 ± 6 | 97.4 ± 1.4 |
| 1.25 µg/ml | 111.2 ± 6.6 | 119.1 ± 0.2 |

The cytotoxic activity of the $^{85}$Rb-enriched rubidium salt of N-benzoyl-N'-(4-toluenesulfonyl)-o-phenylenediamine of formula I was evaluated in the following experiment.

Materials and Methods: Mouse melanoma cells (MM-4 cell line) were seeded into 96-well plates (TPP, Italy) in DMEM (High Glucose w/L-Glutamine w/o Sodium Pyruvate; Biowest, France) supplemented with 10% newborn calf serum (Biowest, France) and 40 mg/ml gentamicin (Sigma, USA) at a seeding density of $5 \times 10^4$ cells/ml. The cells were then cultured in an incubator with a humidified atmosphere of 5% CO$_2$ in air at 37° C. 24 hours after the cells were seeded, a compound according to the invention that comprises $^{85}$Rb-enriched rubidium salt of N-benzoyl-N'-(4-toluenesulfonyl)-o-phenylenediamine of formula I was added into the appropriate wells. $^{85}$Rb$_e$–E2 was used at the following doses: 2.0 µg/ml, 1.0 µg/ml, 0.5 µg/ml (each is the final concentration of $^{85}$Rb$_e$ after addition to the well). The cytotoxic effect was determined by counting the number of live cells observed after treatment, expressed as a percentage of the number of live cells observed/counted in the control (cells seed in the well and not treated). Control cells were not treated. For each concentration, the experiment was carried out twice. The effects of the drugs were evaluated visually, which allowed us to examine the morphological pattern of the cytotoxic action of the drugs, and by staining the cells with crystal violet, followed by OD measurement at an excitation wavelength of 540 nm using a MultiScan spectrophotometer. For comparison, a parallel experiment was carried out with the use of a known antitumor drug cisplatin and a compound of rubidium salt of N-benzoyl-N'-(4-toluenesulfonyl)-o-phenylenediamine of formula I which comprised a naturally-abundant mixture of isotopes of rubidium instead of being enriched for the $^{85}$Rb isotope. The results are presented in Table 1.

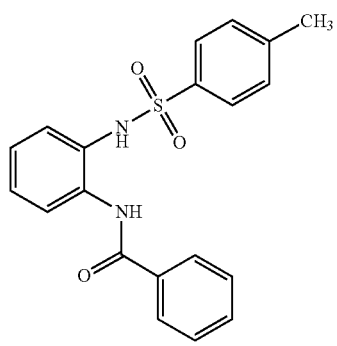

Formula E2

N-benzoyl-N'-(4-toluenesulfonyl)-o-phenylenediamine

TABLE 1

Cytotoxic effect of $^{85}$Rb-enriched and non-$^{85}$Rb-enriched rubidium salt of N-benzoyl-N'-(4-toluenesulfonyl)-o-phenylenediamine of formula I (cells used were Mouse melanoma cells (MM-4 cell line))

| Dosage of $^{85}$Rb$_e$ as E2 + $^{85}$Rb$_e$, μg/ml of $^{85}$Rb$_e$ | Number of cells after their treatment with the drug, % |
|---|---|
| 2.0 | 6.4 ± 0.3 |
| 1.0 | 8.3 ± 0.5 |
| 0.5 | 32.3 ± 0.7 |

| Dosage of Rb as E2 + Rb (naturally-abundant mixture of isotopes), μg/ml | Number of cells after their treatment with the drug, % |
|---|---|
| 2.0 | 62.1 ± 0.8 |
| 1.0 | 84.9 ± 0.9 |
| 0.5 | 90.6 ± 0.9 |

| Dosage of cisplatin, μg/ml | Number of cells after their treatment with the drug, % |
|---|---|
| 10 μg/ml | 2.6 ± 1.4 |
| 5 μg/ml | 13.8 ± 1.2 |
| 2.5 μg/ml | 24.6 ± 5.2 |
| 1.0 μg/ml | 51.7 ± 6.9 |
| 0.5 μg/ml | 84 ± 3.3 |

As can be seen from the data presented, the efficacy of the agent of the invention, which comprises the $^{85}$Rb-enriched rubidium salt of N-benzoyl-N'-(4-toluenesulfonyl)-o-phenylenediamine at a dose of 0.5-2.0 μg rubidium/ml was comparable to cisplatin at a dose of 1.0-10 m/ml in an in vitro model and exceeded the efficacy of the cisplatin used at a dose of 0.5-5 μg/ml. The study has shown that the composition that contained the rubidium salt of N-benzoyl-N'-(4-toluenesulfonyl)-o-phenylenediamine of formula I, which comprises a naturally-abundant mixture of isotopes of rubidium instead of being enriched for $^{85}$Rb, and did not contain the $^{85}$Rb-enriched rubidium salt, had a significantly lower activity against tumor cells.

Example 2. In Vitro Study of the Cytotoxic/Cytostatic Activity of the Composition Comprising the $^{85}$Rb-Enriched Rubidium Salt of N-Benzoyl-N'-(4-Toluenesulfonyl)-o-Phenylenediamine Compound of Formula I and Antitumor Drugs (AD) in B16 Melanoma Cells In the in vitro experiment, the cytotoxic activity of the composition of the invention was studied in relation to the concentration of the $^{85}$Rb-enriched rubidium salt of N-benzoyl-N'-(4-toluenesulfonyl)-o-phenylenediamine of formula I and antitumor drugs ("ADs") with different mechanisms of action. The experiment allowed us to identify the phase-dependent effects of the combined action of the drugs and to avoid undesirable combinations and dosing schedules thereof in the future. Accordingly, additional controls were used in each case to objectively evaluate the results. Evaluation of the effects of the drugs was carried out visually, which allowed us to determine the morphological picture of the cytotoxic action of the drugs, and by staining the cells for quantitative expression of the results.

Materials and Methods: Mouse B16 melanoma cells (MM-4 cell line) were seeded into 96-well plates (TPP, Italy), in DMEM (Biowest, France) supplemented with 10% newborn calf serum (Biowest, France) and 40 mg/ml gentamicin (Sigma, USA) at a seeding density of 5×10$^4$ cells/ml. The cells were then cultured in an incubator with a humidified atmosphere of 5% $CO_2$ in air at 37° C. 24 hours after the cells were seeded, the said composition, which contained various ratios and/or concentrations of the components used, was added into the appropriate wells. The cells then were incubated at 37° C. and 5% $CO_2$ for an additional 72 hours (96 hours in total after the cells were seeded). The following ADs were used in the experiment:

1) Dacarbazine, Medac, GmbH, Germany
2) Paclitaxel, Actavis, Italy
3) Doxorubicin, Ebewe, Austria
4) Vinorelbine (Vinorelsin), Actavis, SindolPharma, Romania
5) Cisplatinum (also referred to as "cisplatin"), Ebewe, Austria The results of the experiment were assessed visually, and the number of cells was determined by staining the cells with crystal violet, followed by OD measurement at an excitation wavelength of 540 nm using a Multi Skan microplate spectrophotometer.

The effects of the complex action of various doses of the investigated substances were evaluated using the concept of synergistic, additive and antagonistic effects of the drugs. The mathematics are detailed below. In short, an additive effect—the effect of the composition (E2+$^{85}$Rb$_e$ and AD)—is equal to the sum of the effects of each separate substance. A synergistic effect—the synergy of the two preparations (E2+$^{85}$Rb$_e$ and AD)—is characterized by the fact that the sum of the effects significantly exceeds the sum of the effect of each individual substance. An antagonistic effect—the pure cytotoxic/cytostatic effect of the interaction of the two preparations (E2+$^{85}$Rb$_e$ and AD) on tumor cells—is equal to zero (does not exceed the effect produced by each substance individually).

The effects were calculated using the Chou-Talalay method according to the following equation ("CI" refers to the "combination index") (see T.-C. Chou, Cancer Res. 70: 440-46 (Jan. 15, 2010):

$$CI=(D)1/(Dx)1+(D)2/(Dx)2+(D)1\times(D)2/(Dx)1/(Dx)2,$$
where (Dx)1 and (Dx)2 are the doses of preparations 1 and 2 that suppress growth of tumor cells by X % when used each individually; and (D)1 and (D)2 are the doses of preparations 1 and 2 that suppress growth of tumor cells by X % when used in combination.

Figure 18:
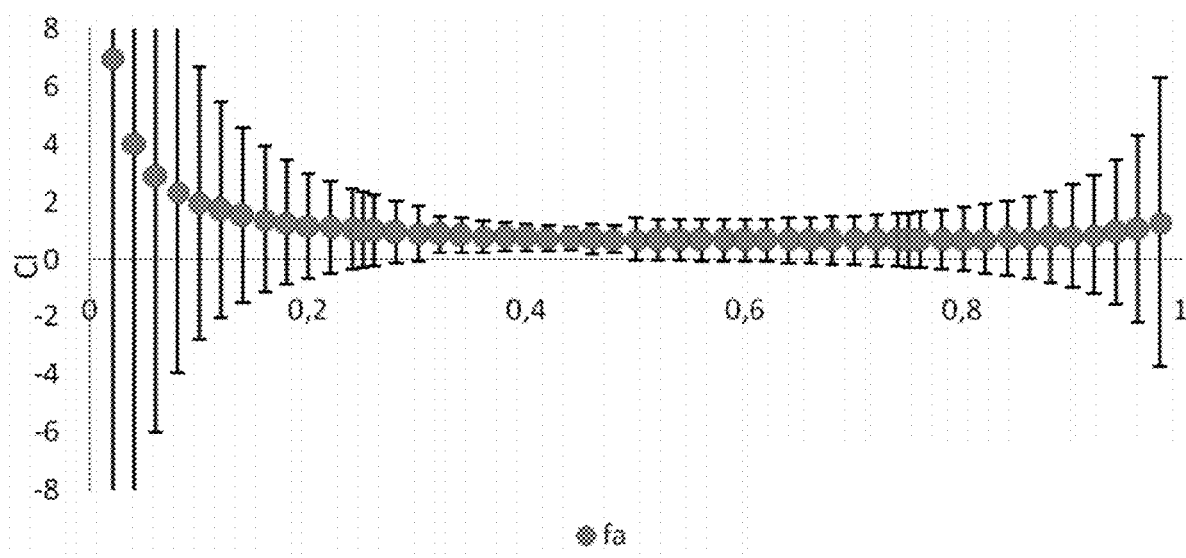
FIG. 18 shows distribution of the combination index CI (the diagram shows 95% confidence interval CI).

(As an example). The diagram (FIG. 18) shows the variation levels CI

TABLE (As an example). Scale of direction and forces of interactions of biologically active substances (physical factors) by Chou-Talalay

| Range CI | Description |
|---|---|
| <0.10 | Very strong synergy |
| 0.10-0.30 | Strong synergies |
| 0.30-0.70 | Synergism |
| 0.70-0.85 | Moderate synergies |
| 0.85-0.90 | Weak Synergy |
| 0.90-1.10 | Additive effect |
| 1.10-1.20 | Weak antagonism |
| 1.20-1.45 | Moderate antagonism |
| 1.45-3.30 | Antagonism |
| 3.30-10.00 | Strong antagonism |
| >10.00 | Very strong antagonism |

A CI of 1 indicates that the preparations have an additive effect when administered together.

For example, in the above Table:

A CI<1 indicates a synergistic effect and CI>1 indicates an antagonistic effect.

Tables 2-6 below shows the findings of the study.

Tables 2-6. Cytotoxic/Cytostatic Activity of the Composition Comprising $E2+^{85}Rb_e$ and AD (Abbreviations Explained Below Table).

Each table sets forth the % of MM-4 cells that survive in the presence of the drug doses indicated in the in vitro experiments described above. The percentage is expressed as a percentage of the cells measured in the control, which was not treated with either $E2+^{85}Rb_e$ or AD (% of surviving MM-4 cells=100×MM-4 cells that survive in the presence of the drug(s)/untreated MM-4 cells). Where both the $^{85}Rb$-enriched rubidium salt (referred to as "$E2+^{85}Rb_e$") and an AD were administered, they were administered simultaneously. Table 2 data indicating synergy are presented in chart form in FIG. 1; Table 3 data indicating synergy are presented in chart form in FIG. 2; Table 5 data indicating synergy are presented in chart form in FIG. 3. FIGS. 1-8 do not include the error bars indicated in the text or Tables. For clarity, data indicating additive or antagonistic interactions between the AD and the $^{85}Rb$-enriched rubidium salt are omitted from the FIGS.

In the Tables, the following abbreviations have the following meanings: A: antagonistic effect; D: additive effect; S: synergistic effect.

TABLE 2

Results of experiments with dacarbazine and $E2+^{85}Rb_e$ added simultaneously

| $E2+^{85}Rb_e$ dose (µg/ml) | 0 | Dacarbazine dose | | | | |
|---|---|---|---|---|---|---|
| | | 40 µg/ml | 20 µg/ml | 10 µg/ml | 5 µg/ml | 2.5 µg/ml |
| 0 | | 3.5 ± 0.7 | 7.8 ± 0.5 | 11.6 ± 3 | 18.1 ± 0.2 | 21 ± 2.4 |
| 2 | 6.4 ± 0.3 | 0 (S) | 0 (S) | 0 (S) | 0 (S) | 1.2 ± 1.2 (S) |
| 1 | 8.3 ± 0.5 | 0 (S) | 0 (S) | 0 (S) | 0 (S) | 1 (S) |
| 0.5 | 32.3 ± 0.7 | 1 (S) | 1.3 ± 0.1 (S) | 2.6 ± 0.4 (S) | 3.2 ± 0.2 (S) | 4 ± 0.1 (S) |

TABLE 3

Results of experiments with paclitaxel and $E2+^{85}Rb_e$ added simultaneously

| $E2+^{85}Rb_e$ dose (µg/ml) | 0 | Paclitaxel dose | | | | |
|---|---|---|---|---|---|---|
| | | 3 µg/ml | 30 ng/ml | 15 ng/ml | 7.5 ng/ml | 3 ng/ml |
| 0 | | 1.9 ± 0.2 | 7 ± 0.8 | 16.1 ± 0.6 | 33.4 ± 1.4 | 80 ± 2.3 |
| 2 | 6.4 ± 0.3 | 4.4 ± 0.2 (A) | 8.6 ± 0.6 (A) | 8.4 ± 0.6 (A) | 8.3 ± 0.1 (A) | 5 ± 0.1 (S) |
| 1 | 8.3 ± 0.5 | 2.3 ± 0.8 (A) | 7.4 ± 0.1 (A) | 7.8 ± 0.4 (A) | 7.2 ± 1.1 (A) | 7.1 ± 0.1 (S) |
| 0.5 | 32.3 ± 0.7 | 2.8 ± 0.2 (A) | 10 ± 1.1 (A) | 10.4 ± 1.5 (A) | 10.9 ± 0.2 (A) | 22.7 ± 2.4 (A) |

TABLE 4

Results of experiments with doxorubicin and E2+$^{85}$Rb$_e$ added simultaneously

| E2+$^{85}$Rb$_e$ dose (μg/ml) | Doxorubicin dose | | | | | |
|---|---|---|---|---|---|---|
| | 0 | 500 ng/ml | 300 ng/ml | 200 ng/ml | 175 ng/ml | 150 ng/ml |
| 0 | 0 | 0 | 3.1 ± 0.1 | 9.1 ± 1.1 | 13 ± 0.1 | 14.4 ± 1.1 |
| 2 | 6.4 ± 0.3 | 4.6 ± 1.2 (A) | 6.2 ± 0.2 (A) | 8.2 ± 1.1 (A) | 8.7 ± 0.6 (A) | 7.9 ± 1.7 (A) |
| 1 | 8.3 ± 0.5 | 3.8 ± 0.1 (A) | 8.2 ± 1.4 (A) | 16.6 ± 1.7 (A) | 15.2 ± 1.2 (A) | 16.1 ± 0.1 (A) |
| 0.5 | 32.3 ± 0.7 | 1.9 ± 0.2 (A) | 6.9 ± 1 (A) | 13.6 ± 0.6 (A) | 14.4 ± 0.6 (A) | 14.6 ± 0.2 (A) |

TABLE 5

Results of experiments with vinorelbine and E2+$^{85}$Rb$_e$ added simultaneously

| E2+$^{85}$Rb$_e$ dose (μg/ml) | Vinorelbine dose | | | | | |
|---|---|---|---|---|---|---|
| | 0 | 200 ng/ml | 50 ng/ml | 25 ng/ml | 5 ng/ml | 1 ng/ml |
| 0 | | 1 | 2 ± 1 | 2 ± 0.8 | 9.5 ± 0.5 | 10 ± 0.1 |
| 2 | 6.4 ± 0.3 | 1.9 ± 0.4 (A) | 1.5 ± 0.1 (A) | 2.3 ± 0.5 (A) | 2.2 ± 0.3 (S) | 2 ± 0.1 (S) |
| 1 | 8.3 ± 0.5 | 0 (S) | 0 (S) | 0 (S) | 1.9 ± 0.2 (S) | 3.3 ± 0.3 (S) |
| 0.5 | 32.3 ± 0.7 | 1 (A) | 1 (S) | 1 (S) | 3.2 ± 0.1 (S) | 4.9 ± 0.1 (S) |

TABLE 6

Results of experiments with cisplatinum and E2+$^{85}$Rb$_e$ added simultaneously

| E2+$^{85}$Rb$_e$ dose (μg/ml) | Cisplatinum dose | | | | | |
|---|---|---|---|---|---|---|
| | 0 | 10 μg/ml | 5 μg/ml | 2.5 μg/ml | 1 μg/ml | 0.5 μg/ml |
| 0 | | 2.6 ± 1.4 | 13.8 ± 1.2 | 24.6 ± 5.2 | 51.7 ± 6.9 | 84 ± 3.3 |
| 2 | 6.4 ± 0.3 | 1.9 ± 0.2 (A) | 8.3 ± 1.3 (A) | 8.1 ± 0.8 (A) | 8.1 ± 1.3 (A) | 8 ± 0.2 (A) |
| 1 | 8.3 ± 0.5 | 1.2 ± 0.2 (A) | 7.9 ± 0.5 (A) | 7.8 ± 0.7 (A) | 7.9 ± 0.1 (A) | 8 ± 0.1 (A) |
| 0.5 | 32.3 ± 0.7 | 2.2 ± 0.2 (A) | 11.8 ± 0.7 (A) | 15.3 ± 3.2 (A) | 22.1 ± 0.4 (A) | 22.3 ± 0.3 (D) |

As can be seen from Tables 2-6 above, a synergistic effect was observed in the composition that comprised E2+$^{85}$Rb$_e$ at a dose of 0.5-2.0 μg/ml and dacarbazine at a dose of 2.5 to 40 μg/ml, a synergistic effect of E2+$^{85}$Rb$_e$ and paclitaxel composition was observed with E2+$^{85}$Rb$_e$ at 1.0 μg/ml and 2.0 μg/ml and paclitaxel at 3 ng/ml and the composition comprising E2+$^{85}$Rb$_e$ and doxorubicin showed no synergistic effect. As for E2+$^{85}$Rb$_e$ and vinorelbine composition, the synergistic effect was observed with E2+$^{85}$Rb$_e$ at 0.5-1.0 μg/ml and vinorelbine at 1-200 ng/ml. The composition of E2+$^{85}$Rb$_e$ and cisplatin had an additive effect only in combination of E2+$^{85}$Rb$_e$ and cisplatin both used at a dose of 0.5 μg/ml.

The above results indicate that the composition comprising the $^{85}$Rb-enriched salt of N-benzoyl-N'-(4-toluenesulfonyl)-o-phenylenediamine of formula I at a dose of 0.5-2.0 μg/ml and an antitumor drug selected from the group consisting of dacarbazine (triazene agent) and vinorelbine (vinca alkaloid) at a dose of 1 ng/ml to 40 μg/ml exhibits strong synergism with respect to cytotoxic activity against tumor cells.

Example 3. In Vitro Study of the Effectiveness of the Claimed Method in B16 Melanoma Cells: Measuring the Effect of Two Drugs Administered Sequentially 24 Hours Apart ($^{85}$Rb-Enriched Rubidium Salt First, AD Second (Scheme 1 Below), and AD First, $^{85}$Rb-Enriched Rubidium Salt Second (Scheme 2 Below))

The effectiveness of the method of the invention that comprises administering antitumor drugs and $^{85}$Rb-enriched rubidium salt of N-benzoyl-N'-(4-toluenesulfonyl)-o-phenylenediamine of formula I was measured in the experiment. A study similar to that described in Example 2 was carried out, except that the $^{85}$Rb-enriched rubidium salt and the AD were administered 24 hours apart. Both orders were tested: AD administered first (Scheme 2, below), and AD administered second (Scheme 1, below).

Materials and Methods: Mouse melanoma cells (MM-4 cell line) were seeded into 96-well plates (TPP, Italy), in DMEM (Biowest, France) supplemented with 10% newborn calf serum (Biowest, France) and 40 mg/ml gentamicin (Sigma, USA) at a seeding density of 5×10$^4$ cells/ml. The cells were then cultured in an incubator with a humidified atmosphere of 5% CO$_2$ in air at 37° C. The experiment was carried out in accordance with the three schemes given below. The experiment was started 24 hours after the cells were seeded. For this purpose, the agents used in the method were introduced into the appropriate wells. The following schemes of introduction were used for the study:

Scheme 1) The $^{85}$Rb-enriched rubidium salt of N-benzoyl-N'-(4-toluenesulfonyl)-o-phenylenediamine of formula I was introduced at the first stage in the following amounts: 2.0 μg/ml, 1.0 μg/ml, 0, 5 μg/ml, and one antitumor drug was introduced at the second stage (after 24 hours). The following ADs were used in the experiment:

Dacarbazine, Medac, GmbH, Germany (doses used: 2.5, 5, 10, 20, 40 μg/ml)

Paclitaxel, Actavis, Italy (doses used: 3.0, 7.5, 15, 30 ng/ml, 30 µg/ml)

Doxorubicin Ebewe, Austria (doses used: 150, 175, 200, 300, 500 ng/ml)

Vinorelbine (Vinorelsin), Actavis, SindolPharma, Romania (doses used: 1, 5, 25, 50, 200 ng/ml)

Cisplatinum Ebewe, Austria (doses used: 0.5, 1.0, 2.5, 5.0, 10 µg/ml)

Scheme 2) An AD was introduced at the first stage at doses as indicated in Scheme 1 above and $^{85}$Rb-enriched rubidium salt of N-benzoyl-N'-(4-toluenesulfonyl)-o-phenylenediamine of formula I was introduced at the second stage (after 24 hours) at the following doses: 2.0 µg/ml, 1.0 m/ml, 0.5 m/ml.

After all the agents were added into the wells, the cells were incubated at 37° C. and 5% $CO_2$ for another 72 hours (96 hours in total after the cells were seeded).

As in example 2, the cytotoxic effect was determined as the percentage of the cell number with respect to the control after their treatment in accordance with the claimed method. The effects of the drugs were evaluated visually, which allowed us to examine the morphological pattern of the cytotoxic action of the drugs, and by staining the cells with crystal violet, followed by OD measurement at an excitation wavelength of 540 nm using a Multi Skan microplate spectrophotometer.

The effects of the complex action of various doses of the investigated substances were evaluated using the concept of synergistic, additive and antagonistic effects of the drugs, as for Example 2, and calculating CI as described in Example 2.

Tables 7-16 below show the findings of the study. Each table sets forth the % of MM-4 cells that survived in the presence of the drug doses indicated in the in vitro experiments described above, expressed as a percentage of the cells in the control wells.

Figure 4:
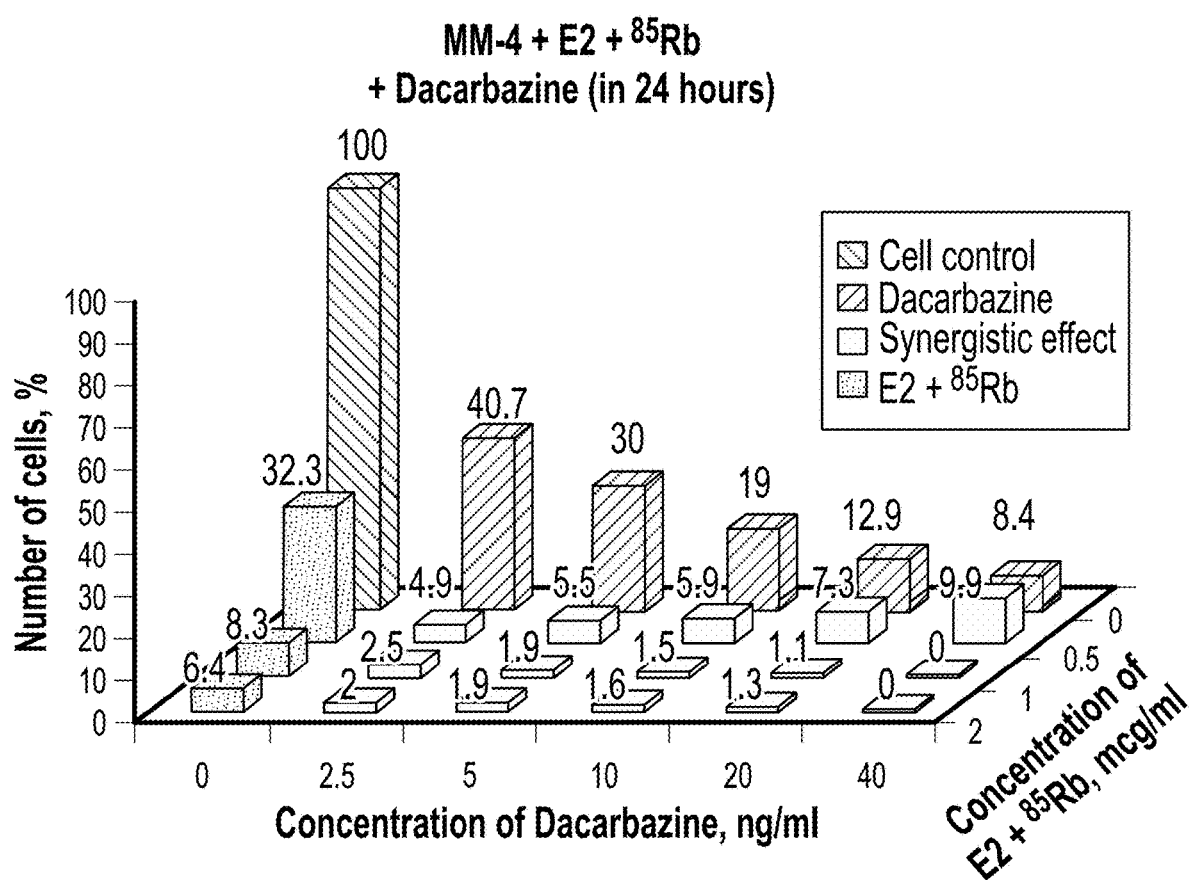
FIG. 4 shows the efficacy data (synergistic effect) in mouse melanoma cells (MM-4 cell line) for a method that comprises administering the $^{85}$Rb-enriched rubidium salt of N-benzoyl-N'-(4-toluenesulfonyl)-o-phenylenediamine followed by the administration (24 hours later) of an antitumor drug dacarbazine (Example 3).

The data from table 7 is displayed in graph form in FIG. 4.

Figure 5:
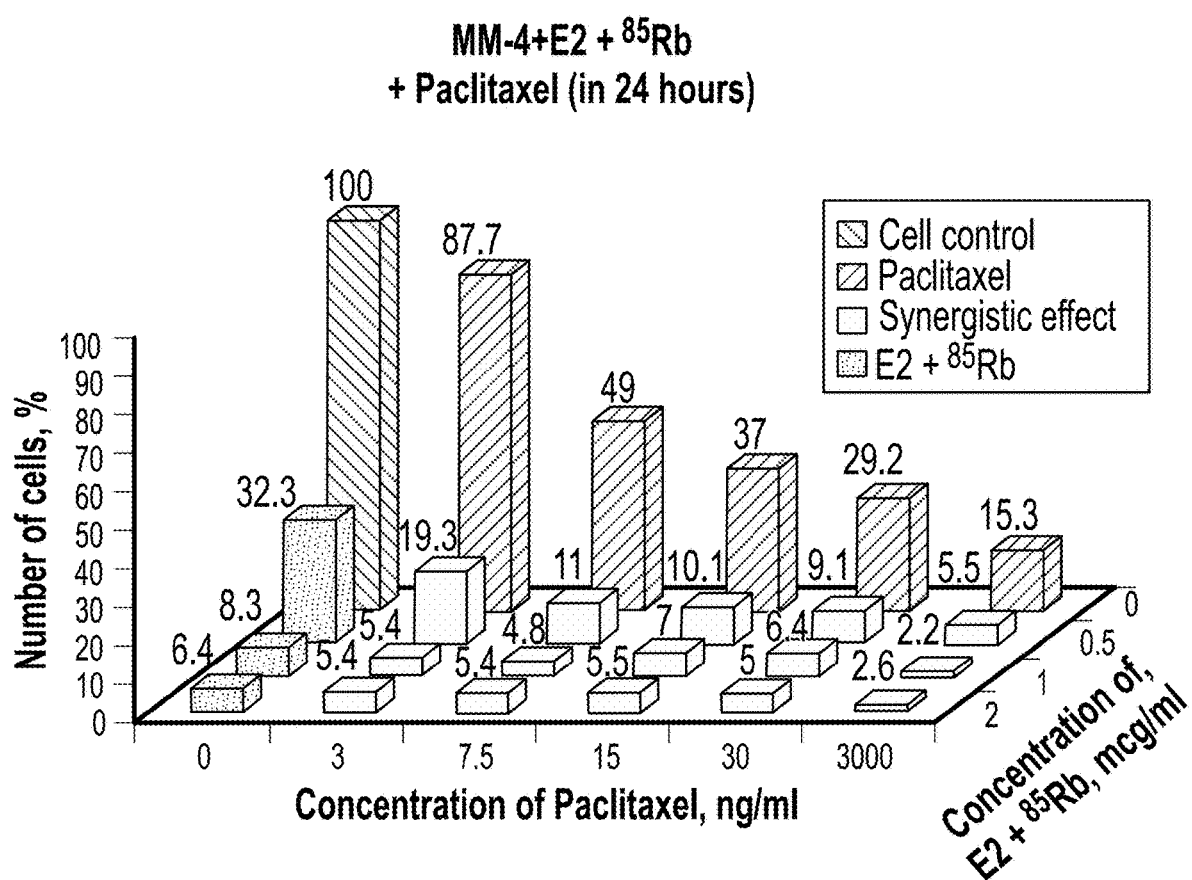
FIG. 5 shows the efficacy data (synergistic effect) in mouse melanoma cells (MM-4 cell line) for a method that comprises administering the $^{85}$Rb-enriched rubidium salt of N-benzoyl-N'-(4-toluenesulfonyl)-o-phenylenediamine followed by the administration (24 hours later) of paclitaxel (Example 3).

The data from table 8 is displayed in graph form in FIG. 5.

Figure 6:
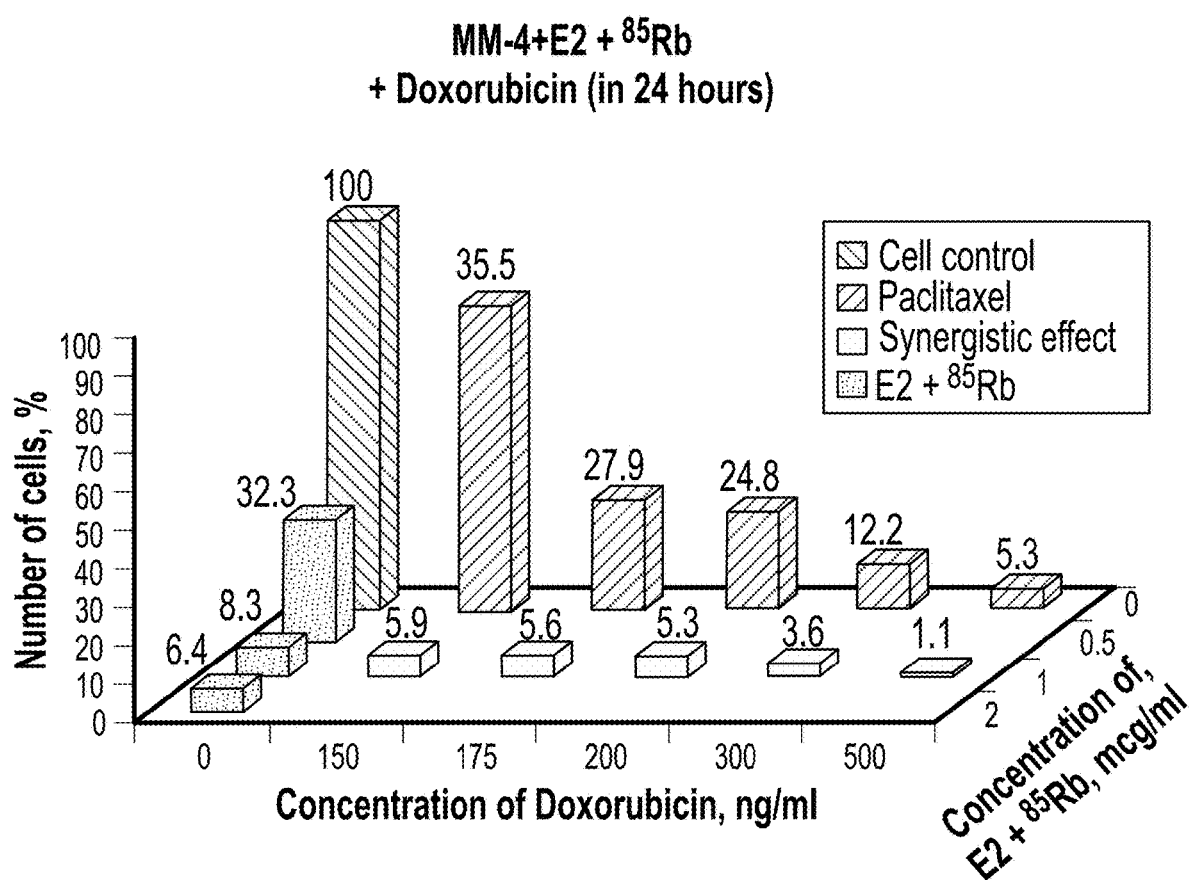
FIG. 6 shows the efficacy data (synergistic effect) in mouse melanoma cells (MM-4 cell line) for a method that comprises administering the $^{85}$Rb-enriched rubidium salt of N-benzoyl-N'-(4-toluenesulfonyl)-o-phenylenediamine followed by the administration (24 hours later) of doxorubicin (Example 3).

The data from table 9 is displayed in graph form in FIG. 6.

Figure 7:
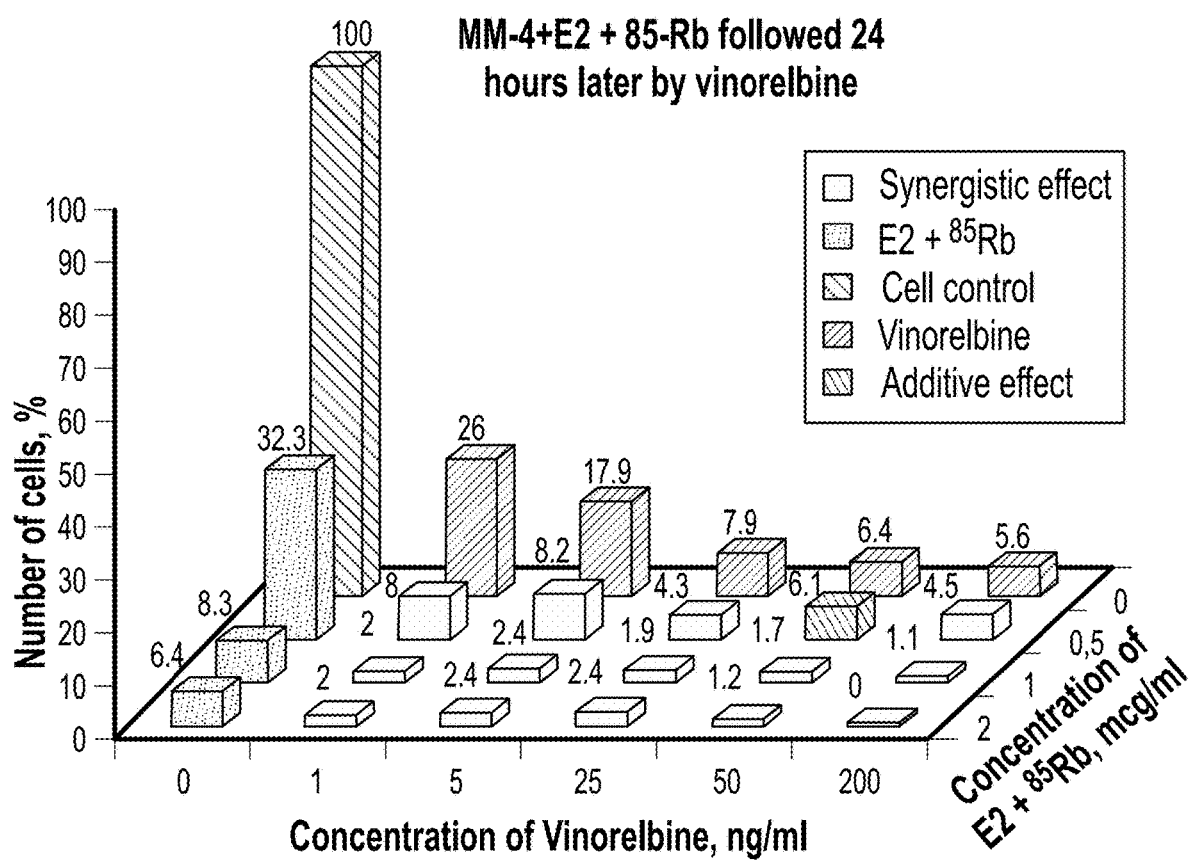
FIG. 7 shows the efficacy data (synergistic effect) in mouse melanoma cells (MM-4 cell line) for a method that comprises administering the $^{85}$Rb-enriched rubidium salt of N-benzoyl-N'-(4-toluenesulfonyl)-o-phenylenediamine followed by the administration (24 hours later) of vinorelbine (Example 3).

The data from table 10 is displayed in graph form in FIG. 7.

Figure 8:
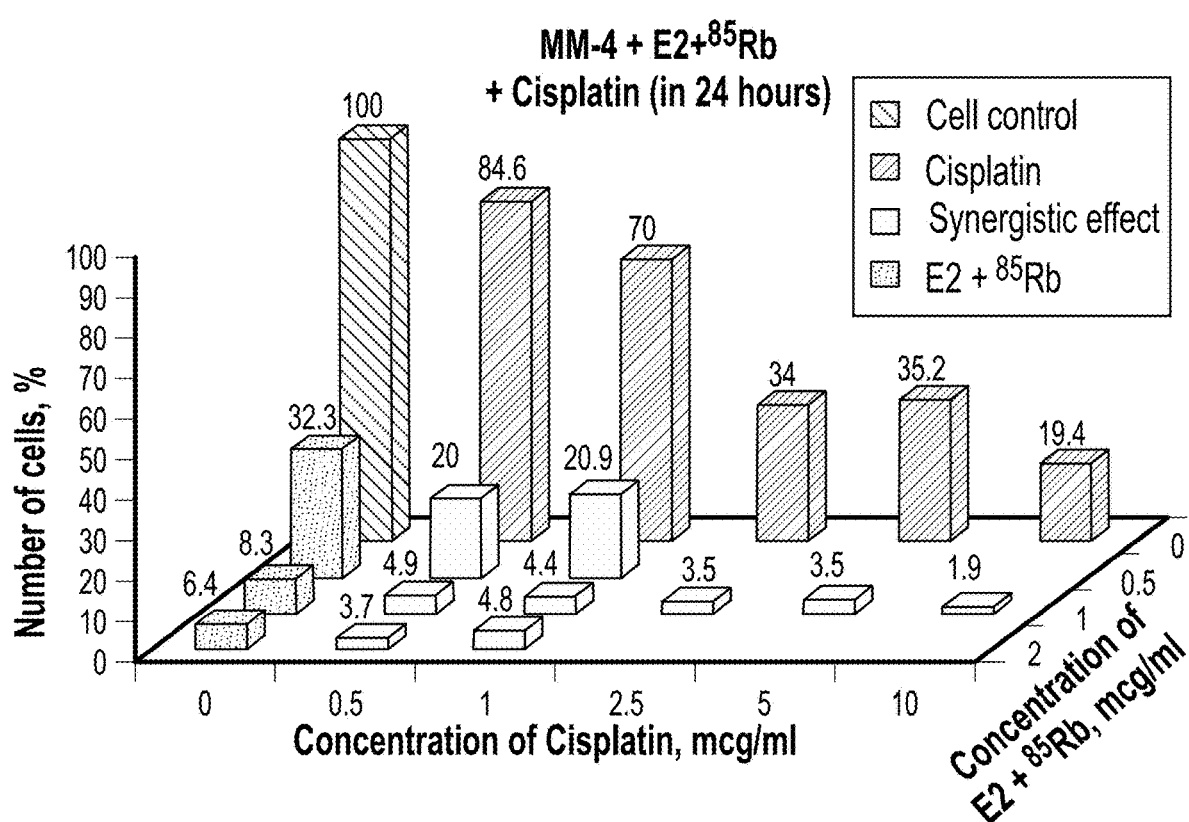
FIG. 8 shows the efficacy data (synergistic effect) for a method that comprises administering the $^{85}$Rb-enriched rubidium salt of N-benzoyl-N'-(4-toluenesulfonyl)-o-phenylenediamine followed by the administration (24 hours later) of cisplatin (Example 3).

The data from table 11 is displayed in graph form in FIG. 8.

The FIGS. do not include the error bars indicated in the text or Tables. For clarity, data indicating additive or antagonistic interactions between the AD and the $^{85}$Rb-enriched rubidium salt are omitted from the FIGS.

In the Tables, the following abbreviations have the following meanings: A: antagonistic effect; D: additive effect; S: synergistic effect.

Tables 7-11. Effectiveness of the Method Comprising Administering E2+$^{85}$Rb$_e$ First and AD Second, 24 Hours after E2+$^{85}$Rb$_e$. (Abbreviations Explained Below Table). In Tables 7-11, the E2+$^{85}$Rb$_e$ Dose Indicated is the Dose of $^{85}$Rb$_e$ in the Form of the $^{85}$Rb$_e$–E2 Salt.

TABLE 7

Results of experiments with dacarbazine added 24 hours after E2+$^{85}$Rb$_e$

| E2+$^{85}$Rb$_e$ dose (µg/ml) | dacarbazine dose | | | | | |
|---|---|---|---|---|---|---|
| | 0 | 40 µg/ml | 20 µg/ml | 10 µg/ml | 5 µg/ml | 2.5 µg/ml |
| 0 | | 8.4 ± 1.2 | 12.9 ± 2.9 | 19 ± 4 | 30 ± 2.4 | 40.7 ± 0.7 |
| 2 | 6.4 ± 0.3 | 0 (S) | 1.3 ± 0.3 (S) | 1.6 ± 0.3 (S) | 1.9 ± 0.6 (S) | 2 ± 0.7 (S) |
| 1 | 8.3 ± 0.5 | 0 (S) | 1.1 ± 0.1 (S) | 1.5 ± 0.4 (S) | 1.9 ± 0.1 (S) | 2.5 ± 0.2 (S) |
| 0.5 | 32.3 ± 0.7 | 4.9 ± 0.1 (S) | 5.5 ± 1.1 (S) | 5.9 ± 0.1 (S) | 7.3 ± 0.1 (S) | 9.9 ± 0.9 (S) |

TABLE 8

Results of experiments with paclitaxel added 24 hours after E2+$^{85}$Rb$_e$

| E2+$^{85}$Rb$_e$ dose (µg/ml) | paclitaxel dose | | | | | |
|---|---|---|---|---|---|---|
| | 0 | 3 µg/ml | 30 ng/ml | 15 ng/ml | 7.5 ng/ml | 3 ng/ml |
| 0 | | 15.3 ± 1.6 | 29.2 ± 4.4 | 37 ± 4.5 | 49 ± 1 | 87.7 ± 6.7 |
| 2 | 6.4 ± 0.3 | 2.6 ± 0.2 (S) | 5 ± 0.2 (S) | 5.5 ± 0.4 (S) | 5.4 ± 0.2 (S) | 5.4 ± 0.3 (S) |
| 1 | 8.3 ± 0.5 | 2.2 ± 0.6 (S) | 6.4 ± 1 (S) | 7 ± 0.5 (S) | 4.8 ± 0.2 (S) | 5.4 ± 0.4 (S) |
| 0.5 | 32.3 ± 0.7 | 5.5 ± 0.1 (S) | 9.1 ± 1.3 (S) | 10.1 ± 0.2 (S) | 11 ± 1.1 (S) | 19.3 ± 0.5 (S) |

TABLE 9

Results of experiments with doxorubicin added 24 hours after E2+$^{85}$Rb$_e$

| E2+$^{85}$Rb$_e$ dose (µg/ml) | doxorubicin dose | | | | | |
|---|---|---|---|---|---|---|
| | 0 | 500 ng/ml | 300 ng/ml | 200 ng/ml | 175 ng/ml | 150 ng/ml |
| 0 | | 5.3 ± 0.9 | 12.2 ± 0.5 | 24.8 ± 5.5 | 27.9 ± 6.9 | 35.5 ± 0.8 |
| 2 | 6.4 ± 0.3 | 1.6 (A) | 4 ± 1.6 (A) | 4.6 ± 0.7 (D) | 7.1 ± 1.8 (A) | 7.4 ± 1.3 (A) |

TABLE 9-continued

Results of experiments with doxorubicin added 24 hours after E2+$^{85}$Rb$_e$

| E2+$^{85}$Rb$_e$ dose (μg/ml) | doxorubicin dose | | | | | |
|---|---|---|---|---|---|---|
| | 0 | 500 ng/ml | 300 ng/ml | 200 ng/ml | 175 ng/ml | 150 ng/ml |
| 1 | 8.3 ± 0.5 | 1.1 ± 0.1 (S) | 3.6 ± 0.1 (S) | 5.3 ± 0.5 (S) | 5.6 ± 0.3 (S) | 5.9 ± 0.3 (S) |
| 0.5 | 32.3 ± 0.7 | 5.2 ± 0.6 (A) | 11.3 ± 0.1 (A) | 12.7 ± 0.8 (A) | 16 ± 0.9 (A) | 19 ± 2.7 (A) |

TABLE 10

Results of experiments with vinorelbine added 24 hours after E2+$^{85}$Rb$_e$

| E2+$^{85}$Rb$_e$ dose (μg/ml) | vinorelbine dose | | | | | |
|---|---|---|---|---|---|---|
| | 0 | 200 ng/ml | 50 ng/ml | 25 ng/ml | 5 ng/ml | 1 ng/ml |
| 0 | | 5.6 ± 0.6 | 6.4 ± 0.4 | 7.9 ± 0.5 | 17.9 ± 0.9 | 26 ± 2.5 |
| 2 | 6.4 ± 0.3 | 0 (S) | 1.2 ± 0.1 (S) | 2.4 ± 0.6 (S) | 2.4 ± 0.6 (S) | 2 ± 0.1 (S) |
| 1 | 8.3 ± 0.5 | 1.1 ± 0.1 (S) | 1.7 ± 0.7 (S) | 1.9 ± 0.9 (S) | 2.4 ± 0.1 (S) | 2 ± 0.5 (S) |
| 0.5 | 32.3 ± 0.7 | 4.5 ± 0.2 (S) | 6.1 ± 1.1 (A) | 4.3 ± 0.3 (S) | 8.2 ± 0.7 (S) | 8 ± 0.4 (S) |

TABLE 11

Results of experiments with cisplatinum added 24 hours after E2+$^{85}$Rb$_e$

| E2+$^{85}$Rb$_e$ dose (μg/ml) | cisplatinum dose | | | | | |
|---|---|---|---|---|---|---|
| | 0 | 10 μg/ml | 5 μg/ml | 2.5 μg/ml | 1 μg/ml | 0.5 μg/ml |
| 0 | | 19.4 ± 0.9 | 35.2 ± 3.3 | 34 ± 2.6 | 70 ± 3.6 | 84.6 ± 3.5 |
| 2 (μg/ml) | 6.4 ± 0.3 | 3 ± 0.1 (D) | 5.9 ± 0.5 (A) | 5 ± 0.2 (A) | 4.8 ± 1 (S) | 3.7 ± 0.7 (S) |
| 1 (μg/ml) | 8.3 ± 0.5 | 1.9 ± 0.2 (S) | 3.5 ± 1.2 (S) | 3.5 ± 0.1 (S) | 4.4 ± 0.7 (S) | 4.9 ± 0.4 (S) |
| 0.5 (μg/ml) | 32.3 ± 0.7 | 7.1 ± 0.9 (A) | 15.8 ± 0.1 (A) | 16.9 ± 1 (A) | 20.9 ± 0.6 (S) | 20 ± 1.5 (S) |

A-antagonistic effect, D-additive effect S-synergistic effect

Tables 12-16. Effectiveness of the Method Comprising Administering AD First and E2+$^{85}$Rb$_e$ Second, 24 Hours after AD. In Tables 12-16, the E2+$^{85}$Rb$_e$ Dose Indicated is the Dose of $^{85}$Rb$_e$ in the Form of the $^{85}$Rb$_e$–E2 Salt.

TABLE 12

Results of experiments with E2+$^{85}$Rb$_e$ added 24 hours after dacarbazine

| E2+$^{85}$Rb$_e$ dose (μg/ml) | dacarbazine dose | | | | | |
|---|---|---|---|---|---|---|
| | 0 | 40 μg/ml | 20 μg/ml | 10 μg/ml | 5 μg/ml | 2.5 μg/ml |
| 0 | | 3.5 ± 0.7 | 7.8 ± 0.5 | 11.6 ± 3 | 18.1 ± 0.2 | 21 ± 2.4 |
| 2 | 17.7 ± 0.8 | 0 (S) | 2 ± 0.2 (S) | 1.8 ± 0.1 (S) | 2 ± 0.1 (S) | 2.9 ± 0.1 (S) |
| 1 | 19 ± 0.5 | 1 ± 0.1 (S) | 2 ± 0.1 (S) | 2 ± 0.1 (S) | 2 ± 0.1 (S) | 2 ± 0.1 (S) |
| 0.5 | 51 ± 1 | 3.5 ± 0.3 (A) | 3.9 ± 0.5 (S) | 4.1 ± 0.6 (S) | 5.6 ± 1.1 (S) | 9.3 ± 1 (S) |

TABLE 13

Results of experiments with E2+$^{85}$Rb$_e$ added 24 hours after paclitaxel

| E2+$^{85}$Rb$_e$ dose (μg/ml) | paclitaxel dose | | | | | |
|---|---|---|---|---|---|---|
| | 0 | 3 μg/ml | 30 ng/ml | 15 ng/ml | 7.5 ng/ml | 3 ng/ml |
| 0 | | 1.9 ± 0.2 | 7 ± 0.8 | 16.1 ± 0.6 | 33.4 ± 1.4 | 80 ± 2.3 |
| 2 | 17.7 ± 0.8 | 5.5 ± 1.5 (A) | 10.2 ± 1 (A) | 12.4 ± 3.8 (A) | 13.3 ± 1.4 (A) | 23.8 ± 2.4 (A) |

TABLE 13-continued

Results of experiments with E2+$^{85}$Rb$_e$ added 24 hours after paclitaxel

| E2+$^{85}$Rb$_e$ dose (µg/ml) | paclitaxel dose | | | | | |
|---|---|---|---|---|---|---|
| | 0 | 3 µg/ml | 30 ng/ml | 15 ng/ml | 7.5 ng/ml | 3 ng/ml |
| 1 | 19 ± 0.5 | 3.3 ± 0.6 (A) | 7 ± 0.9 (A) | 7.5 ± 0.9 (S) | 7.9 ± 0.5 (S) | 11.2 ± 0.9 (S) |
| 0.5 | 51 ± 1 | 4.1 ± 0.3 (A) | 10.7 ± 2.7 (A) | 13.9 ± 1.8 (D) | 13.3 ± 1.7 (S) | 37 ± 3 (A) |

TABLE 14

Results of experiments with E2+$^{85}$Rb$_e$ added 24 hours after doxorubicin

| E2+$^{85}$Rb$_e$ dose (µg/ml) | doxorubicin dose | | | | | |
|---|---|---|---|---|---|---|
| | 0 | 500 ng/ml | 300 ng/ml | 200 ng/ml | 175 ng/ml | 150 ng/ml |
| 0 | | 0 | 3.1 ± 0.1 | 9.1 ± 1.1 | 13 ± 0.1 | 14.4 ± 1.1 |
| 2 | 17.7 ± 0.8 | 4.7 ± 1.3 (A) | 9.7 ± 1.9 (A) | 17.3 ± 0.3 (A) | 17.9 ± 2.7 (A) | 14 ± 0.8 (A) |
| 1 | 19 ± 0.5 | 1.8 ± 0.8 (A) | 4.4 ± 0.1 (A) | 9.8 ± 1.9 (A) | 12.7 ± 2.6 (A) | 12.5 ± 2.7 (A) |
| 0.5 | 51 ± 1 | 0 (A) | 5.3 ± 0.8 (A) | 13.7 ± 0.3 (A) | 13.7 ± 1.1 (A) | 13.1 ± 0.8 (A) |

TABLE 15

Results of experiments with E2+$^{85}$Rb$_e$ added 24 hours after vinorelbine

| E2+$^{85}$Rb$_e$ dose (µg/ml) | vinorelbine dose | | | | | |
|---|---|---|---|---|---|---|
| | 0 | 200 ng/ml | 50 ng/ml | 25 ng/ml | 5 ng/ml | 1 ng/ml |
| 0 | | 1 | 2 ± 1 | 2 ± 0.8 | 9.5 ± 0.5 | 10 ± 0.1 |
| 2 | 17.7 ± 0.8 | 0 (S) | 0 (S) | 1.5 ± 0.5 (S) | 3 ± 0.4 (S) | 3 ± 0.5 (S) |
| 1 | 19 ± 0.5 | 0 (S) | 0 (S) | 1 (S) | 2.7 ± 0.4 (S) | 2.8 ± 0.1 (S) |
| 0.5 | 51 ± 1 | 0 (S) | 0 (S) | 1 (S) | 4 ± 1.5 (S) | 8.1 ± 1.5 (S) |

TABLE 16

Results of experiments with E2+$^{85}$Rb$_e$ added 24 hours after cisplatinum

| E2+$^{85}$Rb$_e$ dose (µg/ml) | cisplatinum dose | | | | | |
|---|---|---|---|---|---|---|
| | 0 | 10 µg/ml | 5 µg/ml | 2.5 µg/ml | 1 µg/ml | 0.5 µg/ml |
| 0 | | 2.6 ± 1.4 | 13.8 ± 1.2 | 24.6 ± 5.2 | 51.7 ± 6.9 | 84 ± 3.3 |
| 2 | 17.7 ± 0.8 | 1.9 ± 0.9 (A) | 10.1 ± 0.1 (A) | 16.4 ± 1.1 (A) | 13.6 ± 1 (S) | 11.4 ± 0.3 (S) |
| 1 | 19 ± 0.5 | 0 (S) | 11 ± 1.7 (D) | 12.1 ± 1.2 (S) | 12.5 ± 1 (S) | 13.2 ± 1.5 (S) |
| 0.5 | 51 ± 1 | 0 (S) | 7.4 ± 0.3 (S) | 15 ± 1.7 (S) | 25.4 ± 2.8 (A) | 25.1 ± 2.7 (S) |

A-antagonistic effect, D-additive effect, S-synergistic effect

As can be seen from the data, the most effective administration regimens tested entailed the separate administration of E2+$^{85}$Rb$_e$ and AD. The most pronounced cytotoxic effect was in the case of delayed administration of E2+$^{85}$Rb$_e$ and AD. In particular, the synergistic effect was observed in many combinations used in the experiment where AD was administered 24 hours after E2+$^{85}$Rb$_e$. When E2+$^{85}$Rb$_e$ was administered 24 hours after AD, a synergistic effect in E2+$^{85}$Rb$_e$ and paclitaxel and E2+$^{85}$Rb$_e$ and cisplatin combinations was observed only with the use of a few specific doses, while combinations with doxorubicin showed only antagonistic effect. The method that entails administering the AD 24 hours after E2+$^{85}$Rb$_e$ is preferred for the drugs tested, although, as mentioned, the reverse order yielded synergy in certain dosage combinations. Another interesting property which was also demonstrated was that some chemotherapeutic drugs produced the best effect at lower concentrations of the compound used, which makes it possible to reduce the amount of an AD to be administered without reducing its efficacy.

Example 4: Reduced Toxicity of Compounds of the Invention

In vitro assessment of the effects of E2+$^{85}$Rb$_e$ on metabolic activity of normal human fibroblasts (MTT assay)

| Concentration of compounds of E2 series | E2 + Rb reference drug | E2 + $^{85}$Rb$_e$ |
|---|---|---|
| | Metabolic activity of cells, % * | |
| 150 µg/ml | 99.3 ± 3.2 | 72.8 ± 2.1 |
| 75 µg/ml | 97.7 ± 7.5 | 67.4 ± 4.7 |
| 38 µg/ml | 98.8 ± 7.1 | 68.5 ± 1.8 |

-continued

| Concentration of compounds of E2 series | E2 + Rb reference drug | E2 + $^{85}Rb_e$ |
|---|---|---|
| | Metabolic activity of cells, % * | |
| 20 µg/ml | 96.8 ± 9.8 | 74 ± 1.3 |
| 10 µg/ml | 104.6 ± 14.2 | 82.5 ± 1.3 |
| 5 µg/ml | 103.4 ± 9.3 | 82.3 ± 3 |
| 2.5 µg/ml | 128.2 ± 8.3 | 84.4 ± 4.6 |
| 1.25 µg/ml | — | 105.1 ± 2.3 |

* in comparison with the control group-100% of living cells

Proliferative and metabolic activity of cells was determined by the colorimetric method.

The metabolic activity of the cells (i.e., the number of living cells) was assessed by MTT staining.

24 hours after the last reagent, the cells were seeded at a concentration of 1×10⁴ cells/well in wells of a 96-well plate in complete DMEM nutrient medium with 10% FBS and 40 µg/ml gentamicin. The cells were cultured in a humidified atmosphere at 5% $CO_2$ and 37° C. for 24 hours. After 24 hours, various doses of experimental substances were added to the respective wells. The cells were incubated at 37° C. and 5% $CO_2$ for an additional 72 hours.

Upon completion of the incubation with the preparations, the proliferative and metabolic activity of the cells in the experiment was evaluated by the colorimetric method by staining MTT cells:

10 µl of the MTT solution (5 mg/ml of the dye in phosphate-buffered saline) was added to each well of the plate; the plate was incubated in a $CO_2$ incubator at 37° C. for 3 hours. After that, the medium was removed from the wells, and the formed tetraformazan crystals were dissolved in 100 µl of dimethylsulfoxide.

When MTT was used, the results were evaluated using a multi-well spectrophotometer at an excitation wavelength of 540 nm. The percentage of viable cells was calculated by the formula:

$$IR=(A540(\text{experiment})/A540(\text{control}))\times 100\%.$$

Thus, the method for the suppression of cancer growth according to the invention can be highly effective in eradicating tumor cells. The observed synergistic effect of the drug interaction makes it possible to control tumor cells using lower concentrations of chemotherapeutic agents than when such agents are used alone.

Example 5: Study on the In Vivo Antitumor Activity of $^{85}Rb_e$–E2 Compound in Combination with a Chemotherapeutic Agent (Cisplatin) Against Mouse Model of Breast Cancer (Ehrlich Ascites Carcinoma)

Brief Description of the Study

Outbred mice were administered Ehrlich ascites carcinoma cells (EAC) intraperitoneally (IP) at a dose of 2.5×10⁵ cells in 0.25 ml of normal saline solution. The compounds under study, 1)$^{85}Rb_e$–E2, was dissolved in deuterium-depleted water and 2) Cisplatin (Teva, the Netherlands), was dissolved in normal saline solution. The drugs were administered starting from the first day after mice were inoculated with tumor cells, using a microinjection syringe, at the following doses: 1)$^{85}Rb_e$–E2 at a dose of 750 µg/mouse (weighing 20 g) in a volume of 0.3 ml as 3 IP injections (1 injection—250 µg/mouse) on the $1^{st}$, $4^{th}$ and $7^{th}$ day of the experiment; 2) Cisplatin at a dose of 4.5 mg/kg or 1.5 mg/kg as 3 IP injections on the $2^{nd}$, $5^{th}$ and $8^{th}$ day of the experiment. The dynamics of tumor growth in the experimental animals was observed (based on the volume of ascites in the peritoneal cavity) after the tumor cell inoculation and for 31 days of the experiment. On the $15^{th}$ and $22^{nd}$ day after IP administration of tumor cells, all the fluid accumulated in each animal's abdomen was extracted and the total number of live/dead cells in each mouse was determined. In addition, some mice were used to assess a survival rate of animals in the experiment.

Goal of the study: in vivo assessment of potential antitumor activity of $^{85}Rb_e$–E2 in combination with DNA-damaging antineoplastic agent Cisplatin against EAC tumor model.

Laboratory animals. 84 outbred female 10 to 12-week old mice weighing 22-26 g were used in the experimental study. The animals were obtained from the animal vivarium at R.E. Kavetsky IEPOR NASU. Before the experiment, all the animals were healthy and demonstrated a normal behavior pattern. The animals were maintained in plastic cages, under natural light-dark cycles, fed standard food and allowed free access to food and tap water.

Tumor model. Ascites strain of Ehrlich ascites carcinoma maintained on outbred mice obtained from the cell and tissue line bank at R.E. Kavetsky IEPOR NASU was used in the experiment. To prepare the strain for injection, tumor cells derived from ascitic fluid were placed in normal saline solution and cellularity of the suspension was assessed in a hemocytometer and adjusted to a concentration of 1·10⁶ cells/ml with saline solution. The tumor cells were inoculated by injecting 250 mcl of cell suspension from the tumor (0.25×10⁶ cells/mouse) into the peritoneal cavity of laboratory animals.

Grouping: The animals were divided into groups as follows (14 mice per group):
1. Group No. 1—control group, EAC+solvent (deuterium-depleted water);
2. Group No. 2—EAC+$^{85}Rb_e$–E2 injected IP at a dose of 4.5 mg/kg (EAC+CP(4.5));
3. Group No. 3—EAC+$^{85}Rb_e$E2 injected IP at a dose of 750 µg/mouse+CP injected IP at a dose of 4.5 mg/kg (EAC+$^{85}Rb_e$–E2+CP(4.5));
4. Group No. 4—EAC+CP injected IP at a dose of 1.5 mg/kg (EAC+CP(1.5));
5. Group No. 5—EAC+$^{85}Rb_e$E2 injected IP at a dose of 750 µg/mouse+CP injected IP at a dose of 1.5 mg/kg (EAC+$^{85}Rb_e$–E2+CP(1.5));
6. Group No. 6—EAC+$^{85}Rb_e$–E2 injected IP at a dose of 750 µg/mouse (EAC+85Rb_e–E2).

Injection Scheme of the Compounds Under Study $^{85}Rb_e$E2 was dissolved in deuterium-depleted water and Cisplatin was dissolved in saline solution.

The drugs were administered IP every other day, using a microinjection syringe, at doses specified above as a series of 3 injections of each compound according to the following scheme: $^{85}Rb_e$–E2 at a dose of 250 µg/mouse weighing 20 g+CP at a dose of 1.5 mg/kg 24 hours later (for groups (EAC+CP(4.5)) and (EAC+$^{85}Rb_e$–E2+CP(4.5)) or 0.5 µg/kg (for groups (EAC+CP(1.5)) and (EAC+$^{85}Rb_e$–E2+CP (1.5)) in a volume of 0.25 ml of saline solution (6 injections in total during 8 days).

The animals in the control group received IP injections of deuterium-depleted water in a volume of 0.3 ml/mouse.

Assessment of Tumor Growth

The tumor growth dynamics in the laboratory animals was observed by daily control of the volume of ascitic fluid in the abdominal cavity of mice starting from the tumor inoculation and for 31 days of the experiment. The dynamics of ascites growth both in control and experimental groups was assessed visually using a 10-point scale, where 0 points were the absence of tumor growth and 10 points were the maximum increase in the size of the abdomen of the mouse with ascites (one point was 0.6 cm of the mean diameter of the mouse abdomen filled with the fluid).

Furthermore, on the $15^{th}$ and $22^{nd}$ day after intraperitoneal injection of tumor cells, all ascitic fluid was removed from the abdomen in 2 or 3 animals from each group by washing their peritoneal cavity with saline solution, and live/dead EAC cells were counted in each mouse using the traditional vital dye trypan blue (HyClon, USA) and a hemocytometer.

The number of cells was determined according to the following formula:

$$X=((a)/80) \times 10^6,$$

where X is the number of cells in 1 ml and a is the number of cells counted in 5 large diagonal squares of the hemocytometer.

7 or 8 mice from each group were used to assess their survival in the experiment. The total lifespan observation time was 31 days from the moment of inoculation of tumor cells.

Statistical data processing. To assess the significance levels of differences in average values between groups Student's t-test and non-parametric Mann-Whitney U test were applied. Calculations were performed using Medstatistic software package.

Results of the Study

Our previous in vitro studies on B16 melanoma cells have shown that successful in terms of cytotoxic effect on tumor cells is the combination of $^{85}Rb_e$-E2 and various antitumor drugs at the lowest possible concentrations. It was shown that the most significant effect was produced by a combined alternating action of $^{85}Rb_e$-E2 and antitumor agents. Therefore, the in vivo antitumor activity of $^{85}Rb_e$-E2 was evaluated in the EAC tumor model both in a mono-regime and in combination with cisplatin, an officially approved antitumor drug. In this experiment, the growth rate of ascites in the control and therapeutic groups was assessed based on the size of abdomen of a mouse with ascites.

The results obtained showed that $^{85}Rb_e$-E2, like cisplatin in a mono-regime, suppressed the EAC development at the initial stages of tumor growth. Thus, $^{85}Rb_e$-E2 has suppressed the growth of carcinoma statistically significantly, namely by an average of 18% by the 15' day after the tumor cells were inoculated, and cisplatin at a dose of 4.5 mg/kg—by an average of 51.3% throughout the observation period, compared with the control group. At the same time, a series of consecutive intraperitoneal injections of $^{85}Rb_e$-E2 at a total dose of 750 μg/mouse and cisplatin at a dose of 4.5 mg/kg resulted in a decrease in the size of experimental tumors by an average of 61% versus control. Such effect of suppression of tumor growth in this group was observed throughout the experiment (Table 17).

Cisplatin in a mono-regime at a dose of 1.5 mg/kg exhibits a statistically significant suppression of tumor growth—by 32%—but only up to the $10^{th}$ day of the experiment. Furthermore, a statistically significant suppression of the experimental tumor growth—by an average of 28% versus control—was observed in the EAC+CP(1.5)+$^{85}Rb_e$-E2 group, and the effect persisted for 21 days after inoculation of tumor cells (Table 17).

TABLE 17

Figure 9:
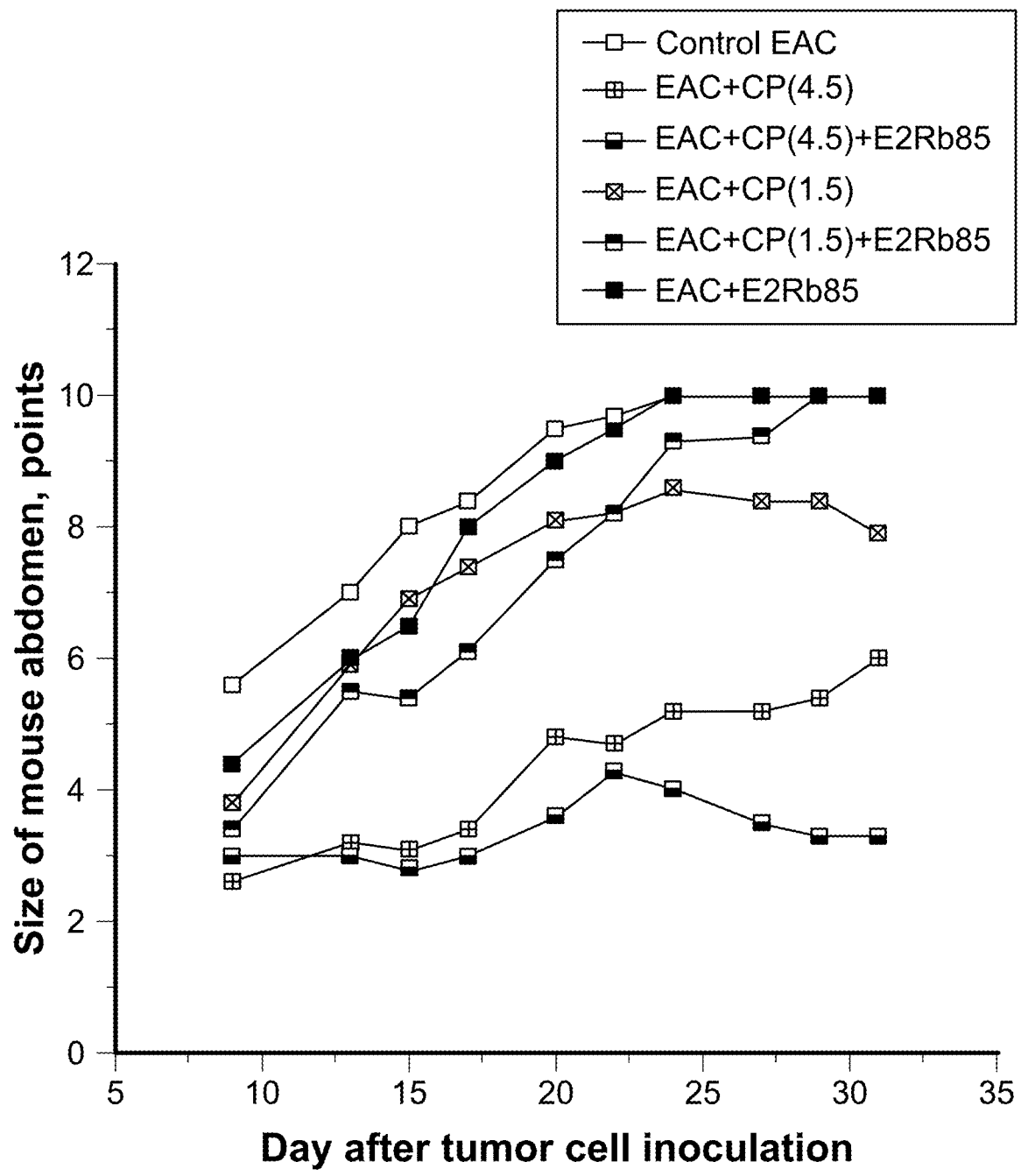
FIG. 9 shows the dynamics of Ehrlich ascites carcinoma ("EAC") growth in a study on the in vivo antitumor activity of $^{85}$Rb$_e$-E2 compound in combination with the chemotherapeutic agent Cisplatin (Example 5).

Dynamics of Ehrlich ascites carcinoma growth in the experiment (analysis of changes in the volumes of ascites in laboratory animals) (see FIG. 9)

| Group of laboratory animals | Day after injection of tumor cells | | | | |
|---|---|---|---|---|---|
| | 9 | 13 | 15 | 17 | 20 |
| | Size of mouse abdomen, points | | | | |
| EAC control | 5.6 ± 0.2 | 7 ± 0.2 | 8 ± 0.4 | 8.4 ± 0.5 | 9.5 ± 0.4 |
| EAC + CP (4.5) | 2.6 ± 0.2* | 3.2 ± 0.3* | 3.1 ± 0.4* | 3.4 ± 0.4* | 4.8 ± 0.5* |
| EAC + CP (4.5) + $^{85}Rb_e$-E2 | 3 ± 0.2* | 3 ± 0.3* | 2.8 ± 0.3* | 3 ± 0.4* | 3.6 ± 0.5* |
| EAC + CP (1.5) | 3.8 ± 0.8* | 5.9 ± 1.1 | 6.9 ± 0.4 | 7.4 ± 0.6 | 8.1 ± 0.6 |
| EAC + CP (1.5) + $^{85}Rb_e$-E2 | 3.4 ± 0.2* | 5.5 ± 0.3* | 5.4 ± 0.4* | 6.1 ± 0.4* | 7.5 ± 0.6* |
| EAC + $^{85}Rb_e$-E2 | 4.4 ± 0.2* | 6 ± 0.3* | 6.5 ± 0.3* | 8 ± 0.6 | 9 ± 0.4 |

TABLE 17-continued

Dynamics of Ehrlich ascites carcinoma growth in the experiment (analysis of changes in the volumes of ascites in laboratory animals) (see FIG. 9)

| Group of laboratory animals | Day after injection of tumor cells | | | | |
|---|---|---|---|---|---|
| | 22 | 24 | 27 | 29 | 31 |
| | Size of mouse abdomen, points | | | | |
| EAC control | 9.7 ± 0.2 | 10 | 10 | died | — |
| EAC + CP (4.5) | 4.7 ± 0.7* | 5.2 ± 0.9* | 5.2 ± 0.9* | 5.4 ± 0.9 | 6 ± 1.3 |
| EAC + CP (4.5) + $^{85}Rb_e$-E2 | 4.3 ± 0.6* | 4 ± 0.6* | 3.5 ± 0.7* | 3.3 ± 1 | 3.3 ± 1 |
| EAC + CP (1.5) | 8.2 ± 0.8 | 8.6 ± 0.8 | 8.4 ± 1 | 8.4 ± 1 | 7.9 ± 1.4 |
| EAC + CP (1.5) + $^{85}Rb_e$-E2 | 8.2 ± 0.7 | 9.3 ± 0.6 | 9.4 ± 0.7 | 10 | 10 |
| EAC + $^{85}Rb_e$-E2 | 9.5 ± 0.4 | 10 | 10 | 10 | 10 |

*p < 0.05 statistically significant difference vs. control group

According to the results of the in vivo study, $^{85}Rb_e$-E2 is able to enhance the antineoplastic activity of cisplatin against the EAC tumor model. Thus, on the $27^{th}$ day of the experiment, when the size of tumors in the control group and in the group where the animals received injections of $^{85}Rb_e$-E2 alone reached 10 points, the mean tumor size in the EAC+CP(4.5) group was 5.2±0.9, while in the EAC+CP(4.5)+$^{85}Rb_e$-E2 group it was 3.5±0.7 points. It should be noted that in the therapeutic groups where mice were given a smaller dose of cisplatin (1.5 mg/kg), the antitumor activity enhancing effect of $^{85}Rb_e$-E2 was also evident: statistically significant inhibition of the EAC growth, as compared with the control, was noted on day 21 after inoculation of the tumor cells, whereas in the groups where the animals were administered the substances at the same doses in a mono-regime this effect was preserved only up to day 9 (EAC+CP(1.5)) and day 15 (EAC+$^{85}Rb_e$-E2) of the experiment (Table 17).

Data on the number of live and dead tumor cells in the ascitic fluid of experimental animals were also used to evaluate the in vivo antitumor activity of the complex of $^{85}Rb_e$E2 compound and cisplatin, a DNA-damaging antitumor agent, against Ehrlich ascites carcinoma. The following results were obtained (Table 18).

TABLE 18

Figure 10:
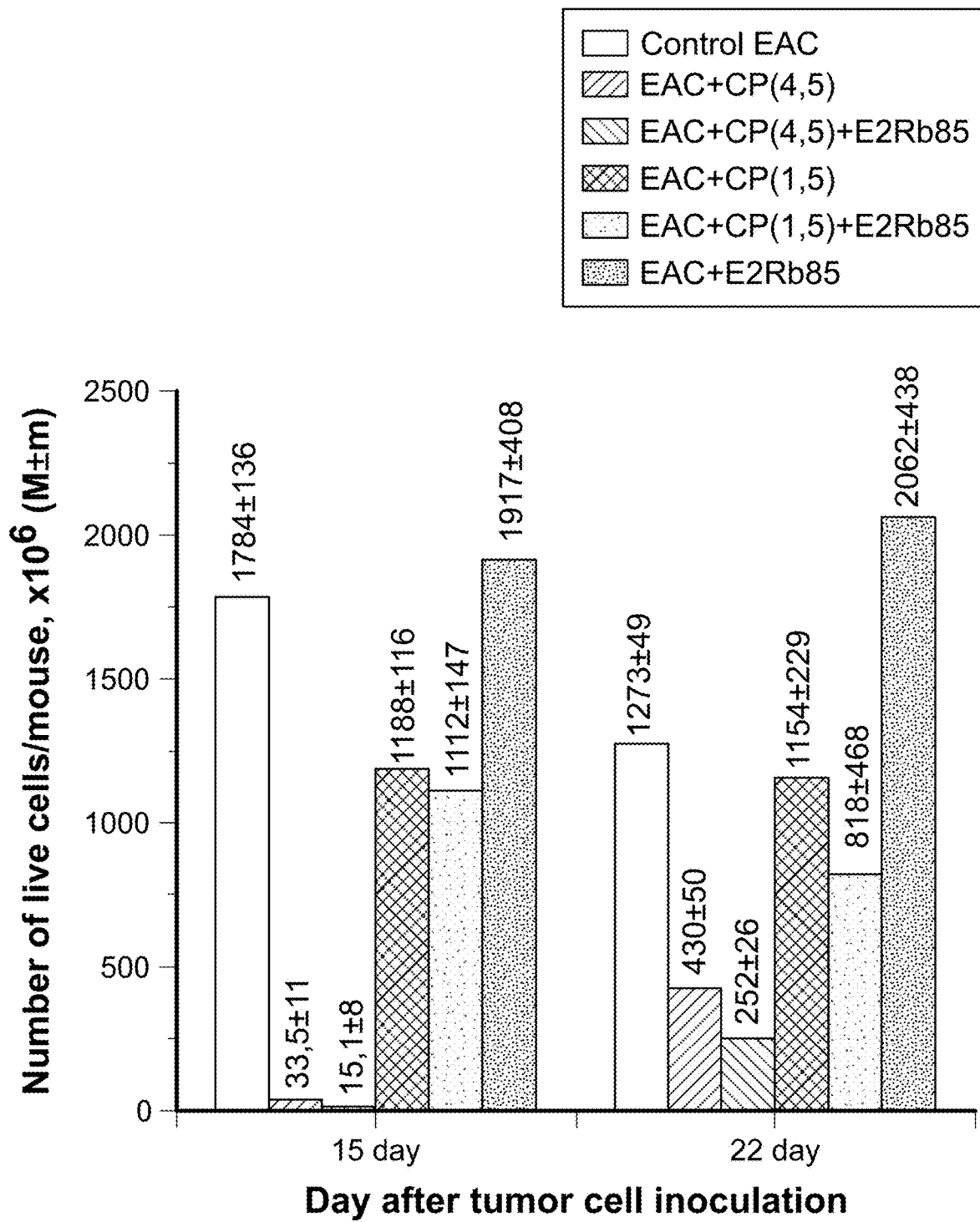
FIG. 10 shows the number of live cells in the ascites on the 15$^{th}$ and 22$^{nd}$ day after inoculation of Ehrlich carcinoma cells (Example 5).
Figure 11:
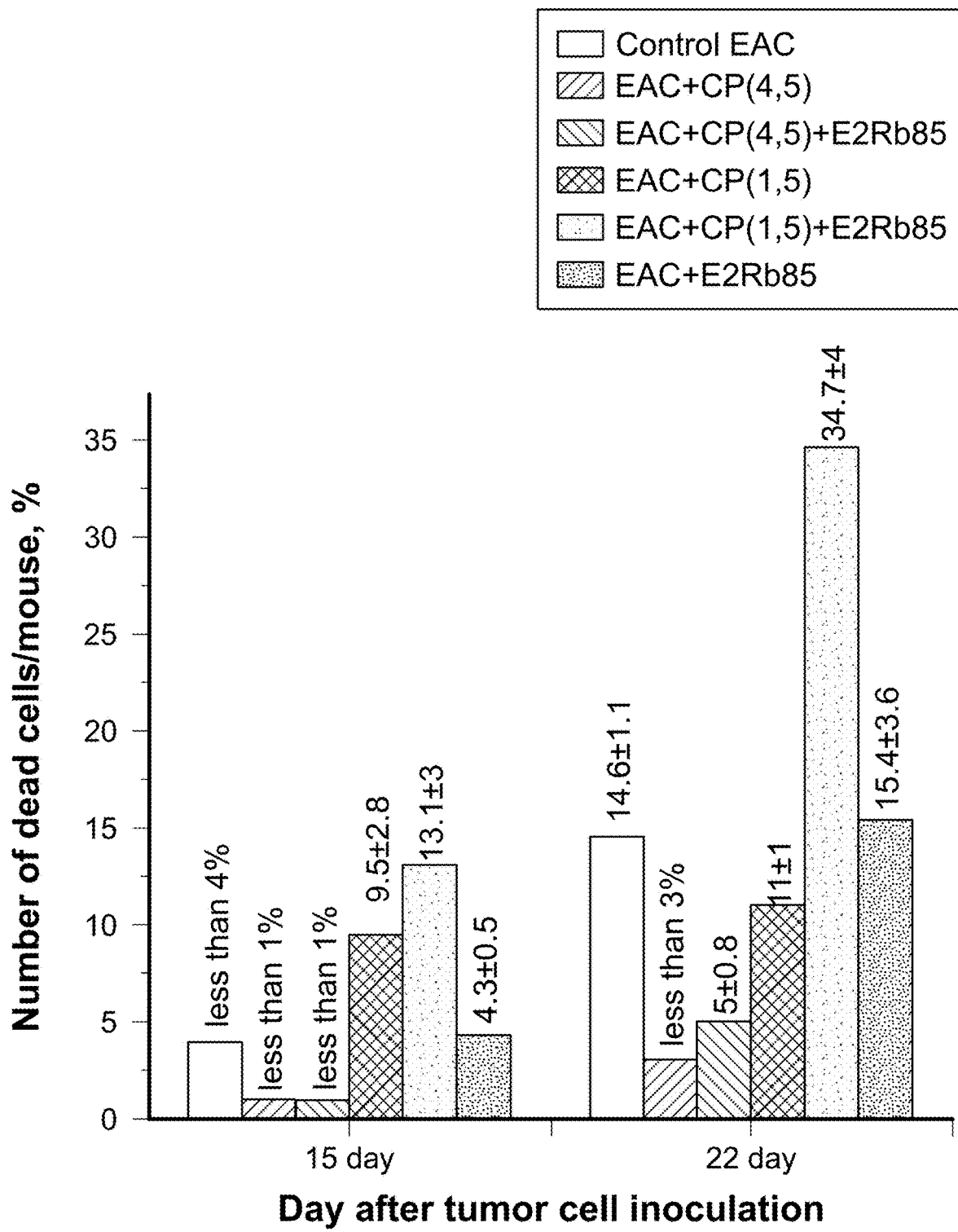
FIG. 11 shows the number of dead cells in the ascites on the 15' and 22$^{nd}$ day after inoculation of Ehrlich carcinoma cells (Example 5).
Figure 12:
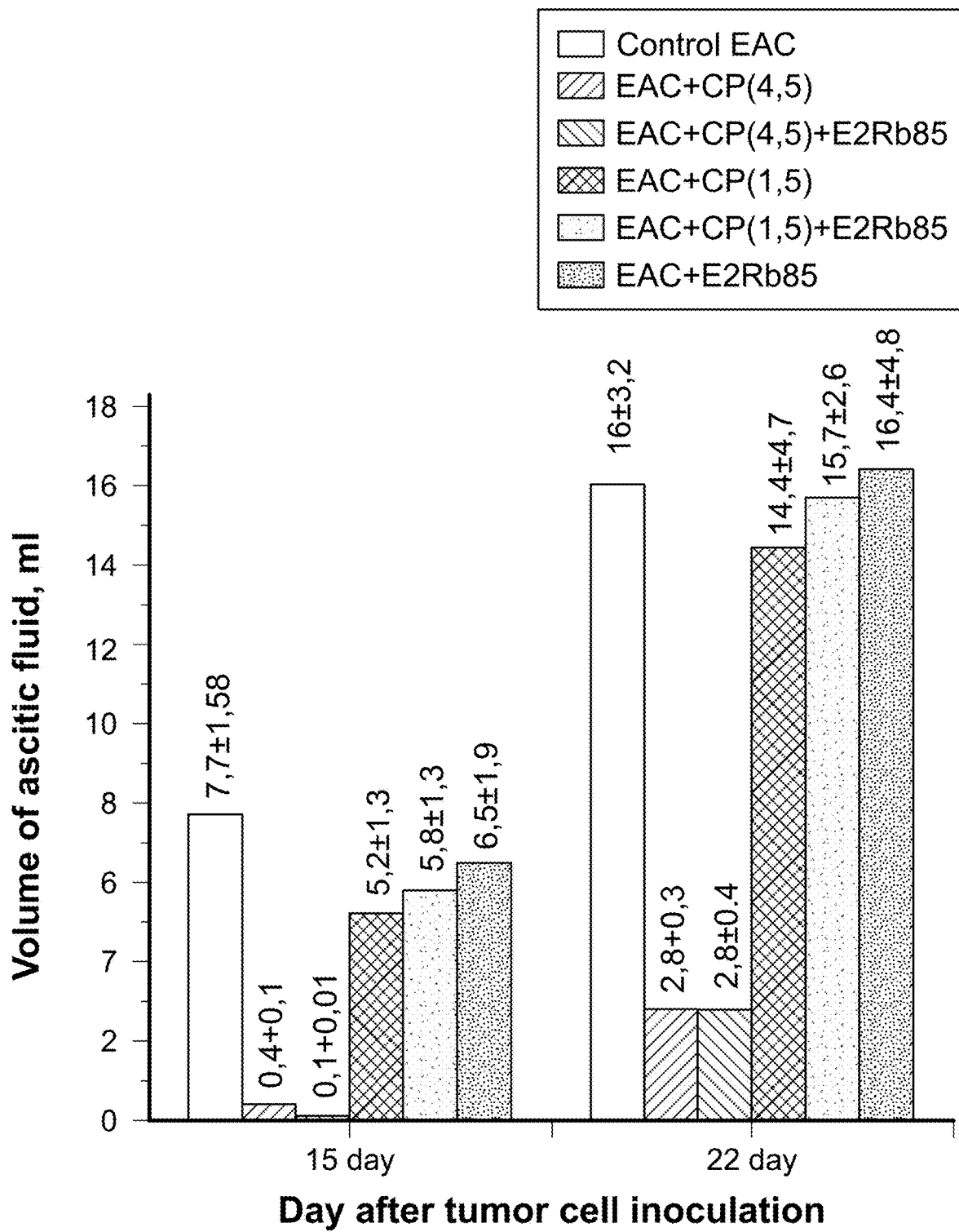
FIG. 12 shows the volume of ascitic fluid on the 15$^{th}$ and 22$^{nd}$ day after inoculation of Ehrlich carcinoma cells (Example 5).
Figure 13A:
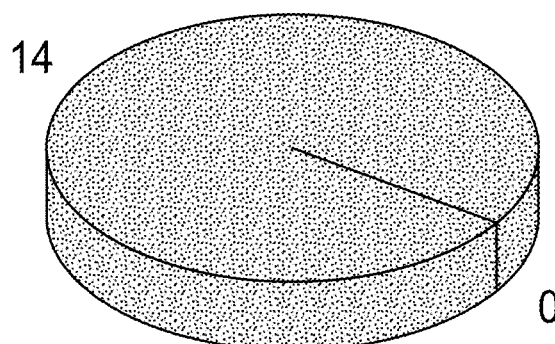
FIG. 13 shows the suppression of EAC tumor growth after it was exposed to the combined action of cisplatin and the experimental compound containing stable isotope Rb$^{85}$ (Example 5).
Figure 13B:
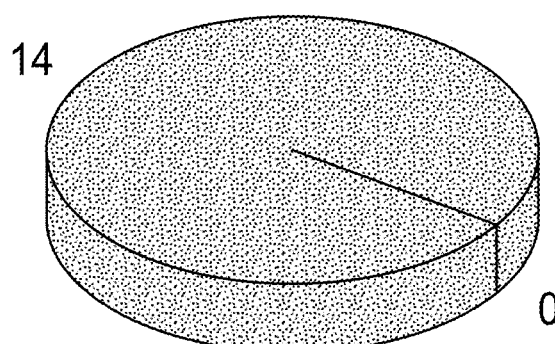
Figure 13C:
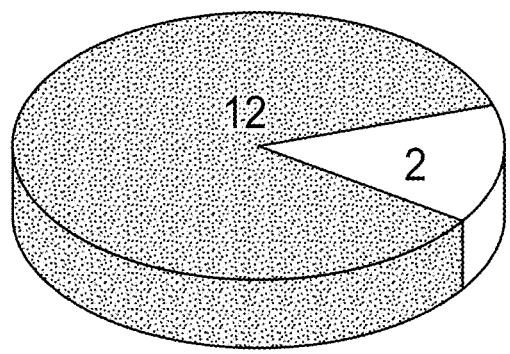
Figure 13D:
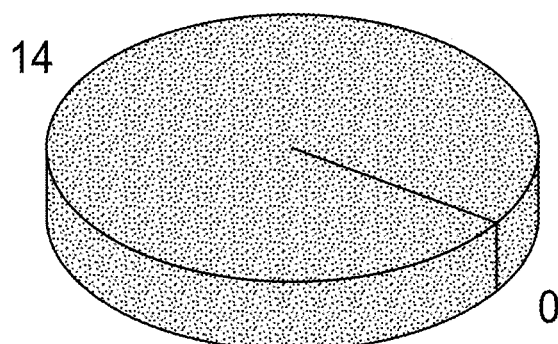
Figure 13E:
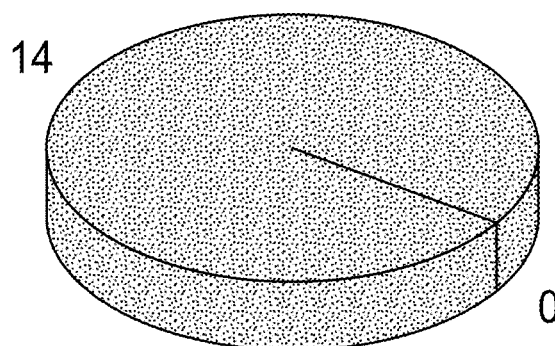
Figure 13F:
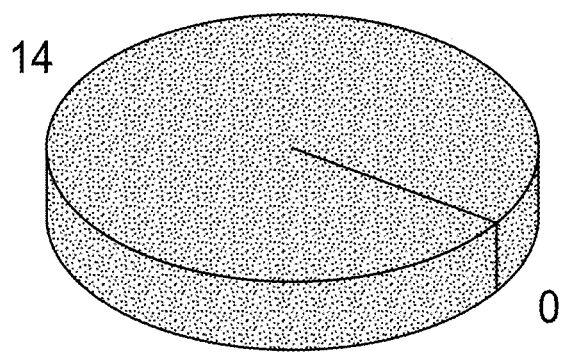
Figure 14:
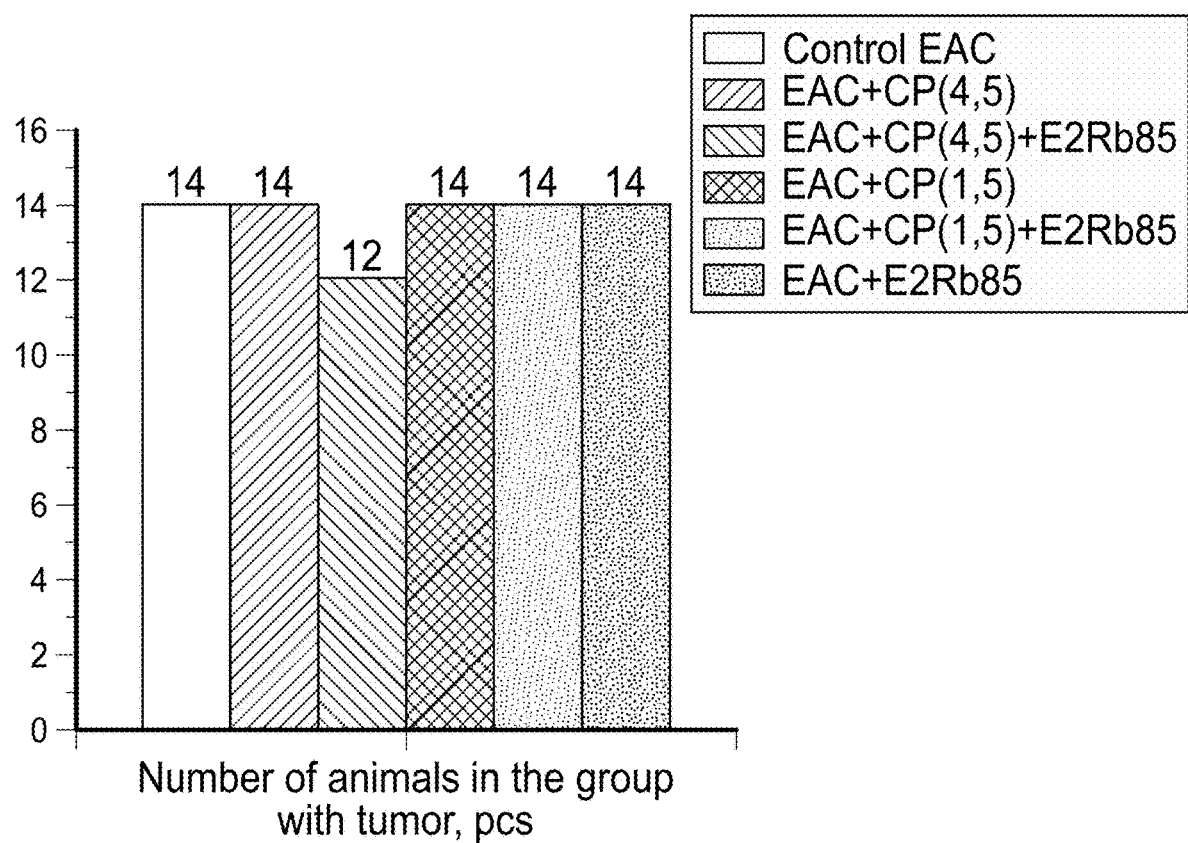
FIG. 14 shows the number of animals in control and experimental groups with tumor (Example 5).
Figure 15:
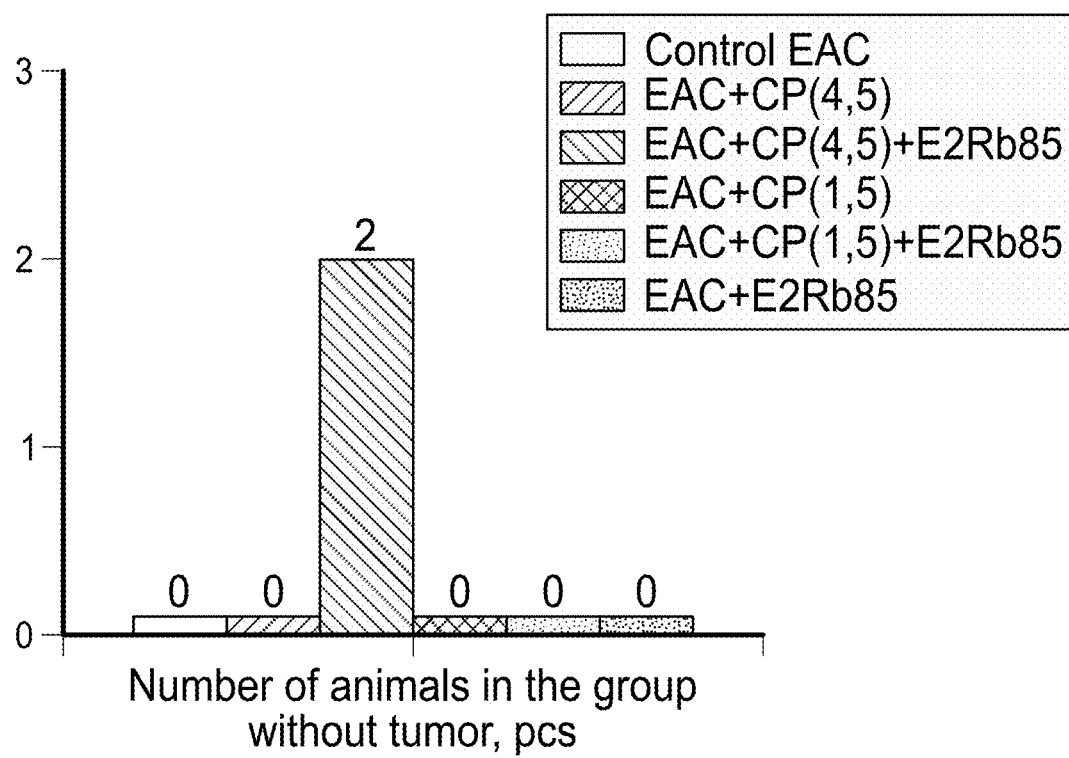
FIG. 15 shows the number of animals in control and experimental groups without tumor (Example 5).
Figure 16:
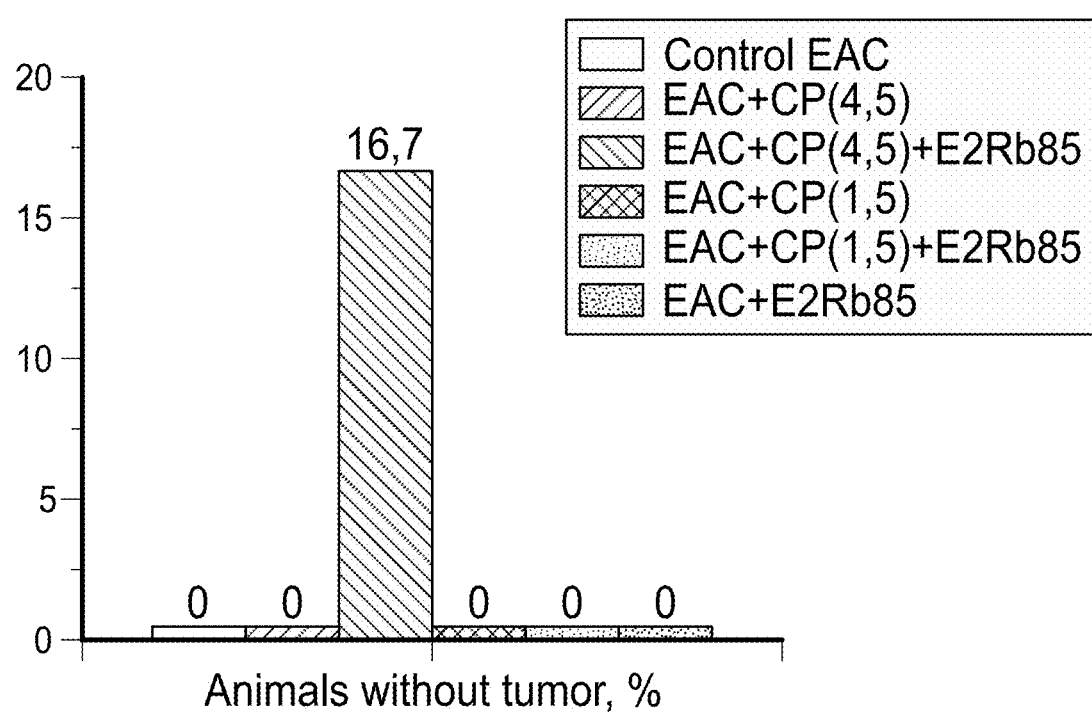
FIG. 16 shows the percentage of animals in control and experimental groups without tumor (Example 5).

Total number of cells in the ascites on the $15^{th}$ and $22^{nd}$ day after inoculation of Ehrlich carcinoma cells (see FIGS. 10-12)

| Group of laboratory animals | Day 15 | | |
|---|---|---|---|
| | Number of live cells/mouse, $\times 10^6$ (M ± m) | Number of dead cells/mouse, % | Volume of ascites, ml |
| EAC control | 1784 ± 136 | <4% | 7.7 ± 1.5 |
| EAC + CP(4.5) | 33.5 ± 11* | <1% | 0.4 ± 0.1* |
| EAC + CP(4.5) + $^{85}Rb_e$-E2 | 15.1 ± 8* | <1% | 0.1 ± 0.1* |
| EAC + CP(1.5) | 1188 ± 116 | 9.5 ± 2.8 | 5.2 ± 1.3 |
| EAC + CP(1.5) + $^{85}Rb_e$-E2 | 1112 ± 147 | 13.1 ± 3 | 5.8 ± 2 |
| EAC + $^{85}Rb_e$-E2 | 1917 ± 408 | 4.3 ± 1.5 | 6.5 ± 2.9 |

TABLE 18-continued

Total number of cells in the ascites on the 15$^{th}$ and 22$^{nd}$ day after inoculation of Ehrlich carcinoma cells (see FIGS. 10-12)

| Group of laboratory animals | Day 22 | | |
|---|---|---|---|
| | Number of live cells/mouse, ×10$^6$ (M ± m) | Number of dead cells/ mouse, % | Volume of ascites, ml |
| EAC control | 1273 ± 479 | 14.6 ± 10.1 | 16 ± 3.2 |
| EAC + CP(4.5) | 430 ± 250 | <3% | 2.8 ± 1.3 |
| EAC + CP(4.5) + $^{85}$Rb$_e$ – E2 | 252 ± 295 | 5 ± 3.8 | 2.8 ± 2.4 |
| EAC + CP(1.5) | 1154 ± 429 | 11 ± 1 | 14.4 ± 8.7 |
| EAC + CP(1.5) + $^{85}$Rb$_e$ – E2 | 818 ± 468 | 34.7 ± 34.7 | 15.7 ± 2.6 |
| EAC + $^{85}$Rb$_e$ – E2 | 2062 ± 438 | 15.4 ± 3.6 | 16.4 ± 4.8 |

*p < 0.05 statistically significant difference vs. control group

Analysis of the results showed that a notable and statistically significant decrease in the number of tumor cells, compared with the control, was observed only on the 15$^{th}$ day of the experiment in groups where mice were injected with cisplatin at a dose of 4.5 mg/kg. It should be noted that the combined administration of the drugs (CP(4.5)+$^{85}$Rb$_e$–E2) at the same dose enhances the effect: in the EAC+CP (4.5) and EAC+CP(4.5)+$^{85}$Rb$_e$–E2 groups, the number of live cells in ascites was approximately ⅓₃ and ¹/₁₁₈ (p<0.05), respectively, of the number of live cells in the control (Table 18). In these groups, on the 22$^{nd}$ day of the experiment, the previously noted trends persisted, but the decrease in the number of live tumor cells, in comparison with the control, was not statistically significant.

At the same time, in groups where the animals received cisplatin at a dose of 1.5 mg/kg, both in a mono-regime and in combination with $^{85}$Rb$_e$–E2 on days 15 and 22 after the EAC cells were inoculated, there were fewer tumor cells in the peritoneal cavity of mice compared with the control group but the difference was statistically insignificant (Table 18).

Analysis of the number of mice in the experimental groups with and without experimental tumors supplements the data on antitumor activity of the experimental compound in mono-regime and in combination with cisplatin. The results presented in Table 19 show that of all therapeutic schemes used in the experiment the most effective series was a series of consecutive IP injections of $^{85}$Rb$_e$–E2 at a total dose of 750 µg/mouse (weighing 20 g) followed by the injection of cisplatin 24 hour later at a total dose of 4.5 mg/kg, since only in this group there were animals (16.7%) with 100% suppression of the EAC growth.

TABLE 19

Suppression of EAC tumor growth after it was exposed to the combined action of cisplatin and the experimental compound containing stable isotope Rb$^{85}$ (and see FIGS. 13-16).

| Group of laboratory animals | Number of animals in the group with tumor | Number of animals in the group without tumor | Animals without tumor, % |
|---|---|---|---|
| EAC control | 14 | 0 | 0 |
| EAC + CP(4.5) | 14 | 0 | 0 |
| EAC + CP(4.5) + $^{85}$Rb$_e$ – E2 | 12 | 2 | 16.7 |
| EAC + CP(1.5) | 14 | 0 | 0 |
| EAC + CP(1.5) + $^{85}$Rb$_e$ – E2 | 14 | 0 | 0 |
| EAC + $^{85}$Rb$_e$ – E2 | 14 | 0 | 0 |

Figure 17:
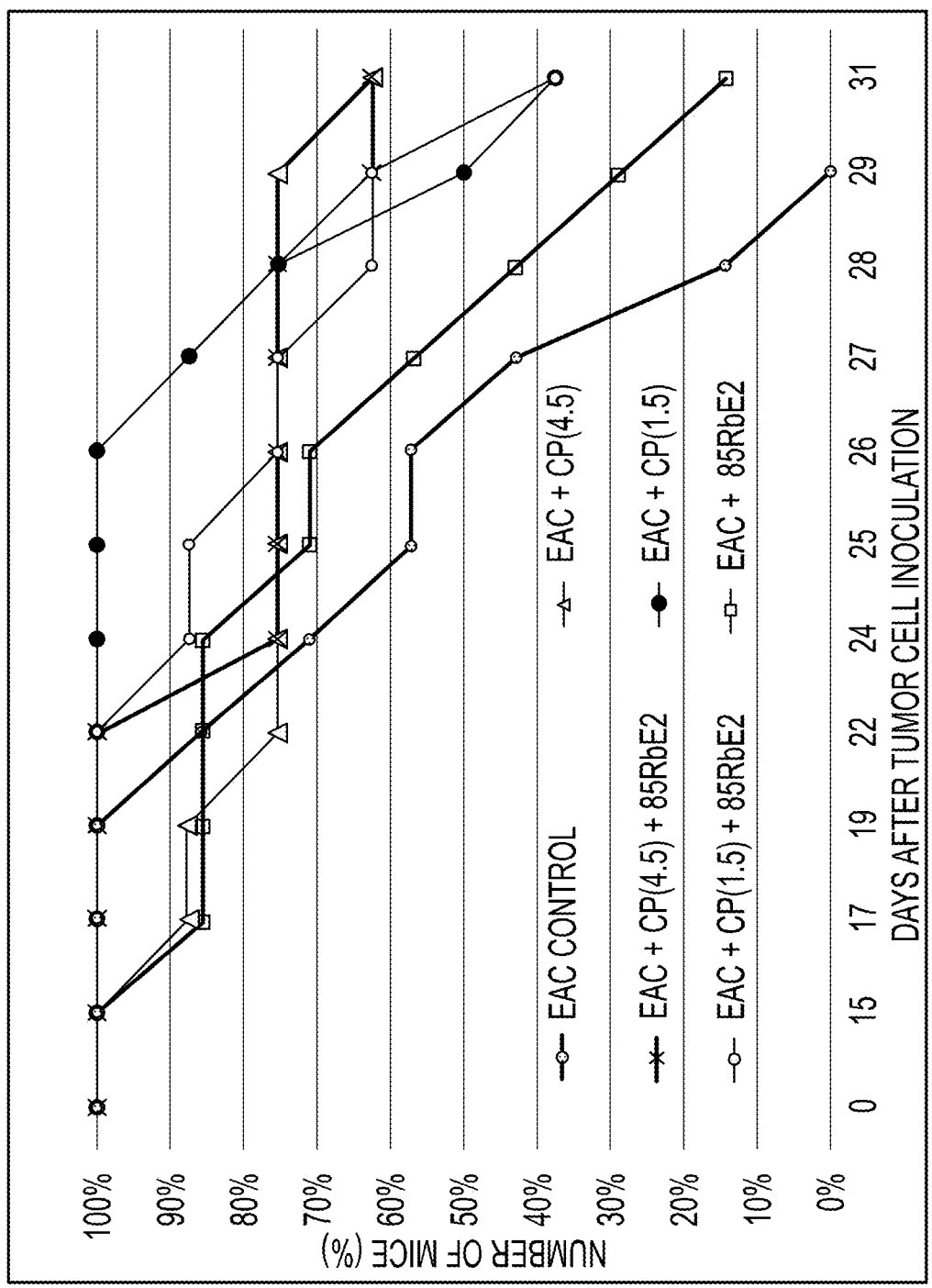
FIG. 17 shows the survival rate of animals in control and experimental groups (Example 5).

Analysis of the survival rate of mice in the experiment showed that the most significant increase in the life span of animals was observed in therapeutic groups where mice received 4.5 mg/kg of cisplatin (FIG. 17). Thus, the last animal in the control group died on the 29$^{th}$ day after introduction of carcinoma cells, while in the EAC+CP(4.5) and EAC+CP(4.5)+$^{85}$Rb$_e$E2 groups, 75% and 62.5% of mice, respectively, remained alive. On day 31 of the experiment, 62.5% of mice survived in these groups. At the same time, in groups where cisplatin was administered at a dose of 1.5 mg/kg in a mono-regime and in combination with $^{85}$Rb$_e$–E2, an increase in the life span of mice was noted as well. Thus, on day 29 of the experiment, in the EAC+CP (1.5) and EAC+CP(1.5)+$^{85}$Rb$_e$–E2 groups, there were 50% and 62.5% of live mice, respectively, and on day 31, there remained 37.5% of the survivors in both groups. It should be noted that a series of IP injections of $^{85}$Rb$_e$E2 alone did not have a significant effect on the survival rate of mice in the experiment.

Conclusion: It has been found that $^{85}$Rb$_e$E2 and cisplatin, when administered in a mono-regime, suppress the EAC development at the initial stages of tumor growth. A statistically significant suppression of experimental tumor growth—by an average of 28% with respect to control—was observed in the EAC+CP(1.5)+$^{85}$Rb$_e$–E2 group for 21 days after the tumor cells were inoculated. According to the results of the in vivo study, $^{85}$Rb$_e$E2 is able to enhance the antineoplastic activity of cisplatin against the EAC tumor model. Thus, on the 27$^{th}$ day of the experiment, when the size of tumors in the control group and in the group where the animals received injections of $^{85}$Rb$_e$E2 alone reached 10 points, the mean tumor size in the EAC+CP(4.5) group was 5.2±0.9, while in the EAC+CP(4.5)+$^{85}$Rb$_e$E2 group it was 3.5±0.7 points. The results also show that a notable and statistically significant decrease in the number of tumor cells, compared with the control, was observed on the 15$^{th}$ day of the experiment in groups where mice were injected with cisplatin at a dose of 4.5 mg/kg, and the combined administration of drugs (CP(4.5)+$^{85}$Rb$_e$–E2) at the same dose enhances the effect: in the EAC+CP(4.5) and EAC+CP(1.5)+$^{85}$Rb$_e$–E2 groups, the number of live cells in ascites was 52 and 119 times smaller (p<0.05), respectively, than in the control.

Analysis of the survival rate of mice in the experiment showed that the most significant increase in the life span of animals was observed in therapeutic groups where mice received 4.5 mg/kg of cisplatin. Thus, the last animal in the control group died on the 29$^{th}$ day after introduction of carcinoma cells, while in the EAC+CP(4.5) and EAC+CP (4.5)+$^{85}$Rb$_e$E2 groups, 75% and 62.5% of mice, respectively, remained alive. On day 31 of the experiment, 62.5% of mice survived in these groups. In groups where cisplatin was administered at a dose of 1.5 mg/kg in a mono-regime and in combination with $^{85}$Rb$_e$–E2, an increase in the life span of mice was noted as well. The data are shown in Table 20 and in FIG. 17.

TABLE 20

| Day after tumor cell inoculation | Experimental groups [Percent (number of mice)] | | |
|---|---|---|---|
| | EAC control | EAC + CP(4.5) | EAC + CP(4.5) + $^{85}$Rb$_e$ – E2 |
| 0 | 100% (7) | 100% (8) | 100% (8) |
| 15 | 100% (7) | 100% (8) | 100% (8) |
| 17 | 100% (7) | 87.5% (7) | 100% (8) |
| 19 | 100% (7) | 87.5% (7) | 100% (8) |
| 22 | 86% (6) | 75% (6) | 100% (8) |
| 24 | 71% (5) | 75% (6) | 75% (6) |
| 25 | 57% (4) | 75% (6) | 75% (6) |
| 26 | 57% (4) | 75% (6) | 75% (6) |
| 27 | 43% (3) | 75% (6) | 75% (6) |
| 28 | 14.3% (1) | 75% (6) | 75% (6) |
| 29 | 0 | 75% (6) | 62.5% (5) |
| 31 | | 62.5% (5) | 62.5% (5) |

TABLE 20-continued

| Day after tumor cell inoculation | Experimental groups [Percent (number of mice)] | | |
|---|---|---|---|
| | EAC + CP(1.5) | EAC + CP(1.5) + $^{85}Rb_e$ – E2 | EAC + $^{85}Rb_e$ – E2 |
| 0 | 100% (8) | 100% (8) | 100% (7) |
| 15 | 100% (8) | 100% (8) | 100% (7) |
| 17 | 100% (8) | 100% (8) | 85.7% (6) |
| 19 | 100% (8) | 100% (8) | 85.7% (6) |
| 22 | 100% (8) | 100% (8) | 85.7% (6) |
| 24 | 100% (8) | 87.5% (7) | 85.7% (6) |
| 25 | 100% (8) | 87.5% (7) | 71% (5) |
| 26 | 100% (8) | 75% (6) | 71% (5) |
| 27 | 87.5% (7) | 75% (6) | 57% (4) |
| 28 | 75% (6) | 62.5% (5) | 43% (3) |
| 29 | 50% (4) | 62.5% (5) | 29% (2) |
| 31 | 37.5% (3) | 37.5% (3) | 14% (1) |

Example 6

Compound 7 was prepared as follows. The same procedure can be used to prepare the other compounds of Formulas 1 and 2, with use of $^{85}Rb_eCl$ or RbCl as appropriate and with starting materials and intermediates comprising the appropriate substituents to obtain the desired product. An alternative synthesis is provided below for when $R_9$ is $OCH_3$.

Phase 1

10.8 g of o-phenylenediamine base were dissolved in 100 ml of isopropyl alcohol and, while maintaining the mixture at room temperature, 200 ml of an alcohol solution of benzenesulfonyl chloride (17.65 g) were added. The resulting mixture was stirred up for 1 hour at room temperature and 0.5 hours at 65-70° C. After cooling, the resulting light-colored precipitate was filtered by thorough washing with cold water to remove the residue of unreacted o-phenylenediamine. The precipitate from the filter was boiled in 10% hydrochloric acid and filtered while hot to remove by-produced bis-dibenzenesulfonyl-o-phenylenediamine. The filtrate was clarified with activated carbon and, after cooling, N-benzenesulfonyl-o-phenylenediamine hydrochloride in the form of fine needle crystals was filtered off (weight per dry matter 7.11 g. Yield 25%).

Phase 2

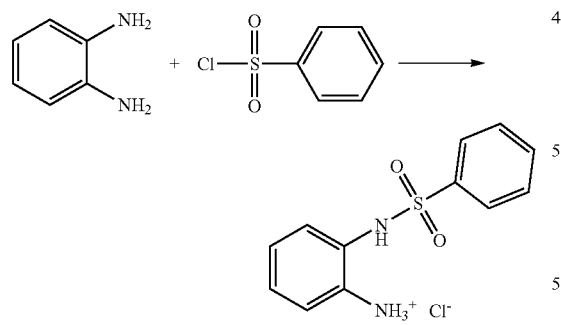

N-benzenesulfonyl-o-phenylenediamine hydrochloride obtained in the first phase (7.11 g) was suspended in 50 ml of toluene and 5.1 g of o-nitrobenzoyl chloride and 5.32 g (7.1 ml) of triethylamine were added. The reaction mixture was boiled under reflux in an oil bath for 3 hours and, after cooling, the precipitate formed was filtered off. The resulting substance was recrystallized from isopropyl alcohol and purified with activated carbon. The yield of dry N-benzenesulfonyl-N'-2-nitrobenzoyl-o-phenylenediamine was 6.45 g (65%).

Phase 3

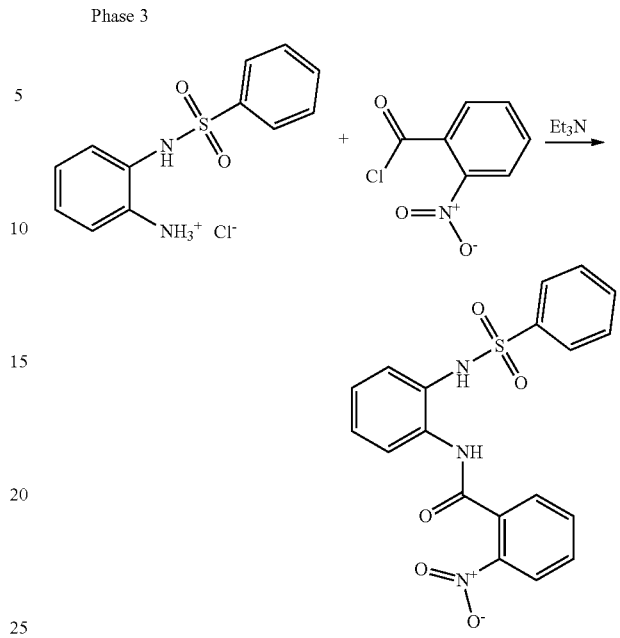

Preparation of aqueous solution of rubidium salt of N-benzenesulfonyl-N'-2-nitrobenzoyl-o-phenylenediamine with a concentration of 0.001 g/ml with $^{85}Rb_e$:

0.073 g of KOH and 0.467 g of N-benzenesulfonyl-N'-2-nitrobenzoyl-o-phenylenediamine were dissolved in 90 ml of deionized water. The solution was stirred up while heating to dissolve the precipitate completely. After being cooled to room temperature, the solution was filtered and 0.1417 g of $^{85}Rb_eCl$ ($^{85}Rb_e$ was 99% $^{85}Rb$) was added, which quickly dissolved. The reaction mixture was stirred up at room temperature for 30 minutes and filtered again. The filtrate was made up to 100 ml with deionized water and used for further studies.

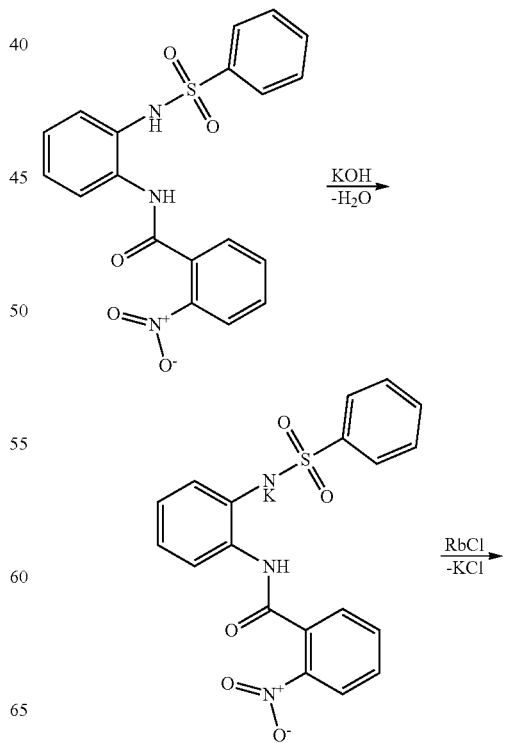

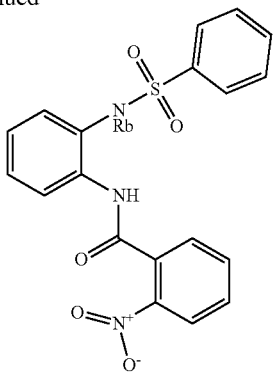

The following methods, among others, can be used to identify the newly synthesized compounds: measurement of the PMR spectra on a Varian VXR 200 spectrometer with respect to TMS in DMSO-$d_6$; measurement of IR spectra (4000-600 $cm^{-1}$) on a Bruker ALPHA FT-IR spectrometer using the ATR accessory; TLC on Silicagel 60 F254 plates (eluent: chloroform); determination of mass spectra using a Kratos MS 890 mass spectrometer, with direct injection of the sample into the ion source at an ionization chamber temperature of 180-250° C. and ionizing electron energy of 70 eV.

When $R_9$ is $OCH_3$, the following alternative synthesis may be used. In the last step, $^{85}Rb_eCl$ can be used instead of RbCl in order to prepare an $^{85}Rb$-enriched product.

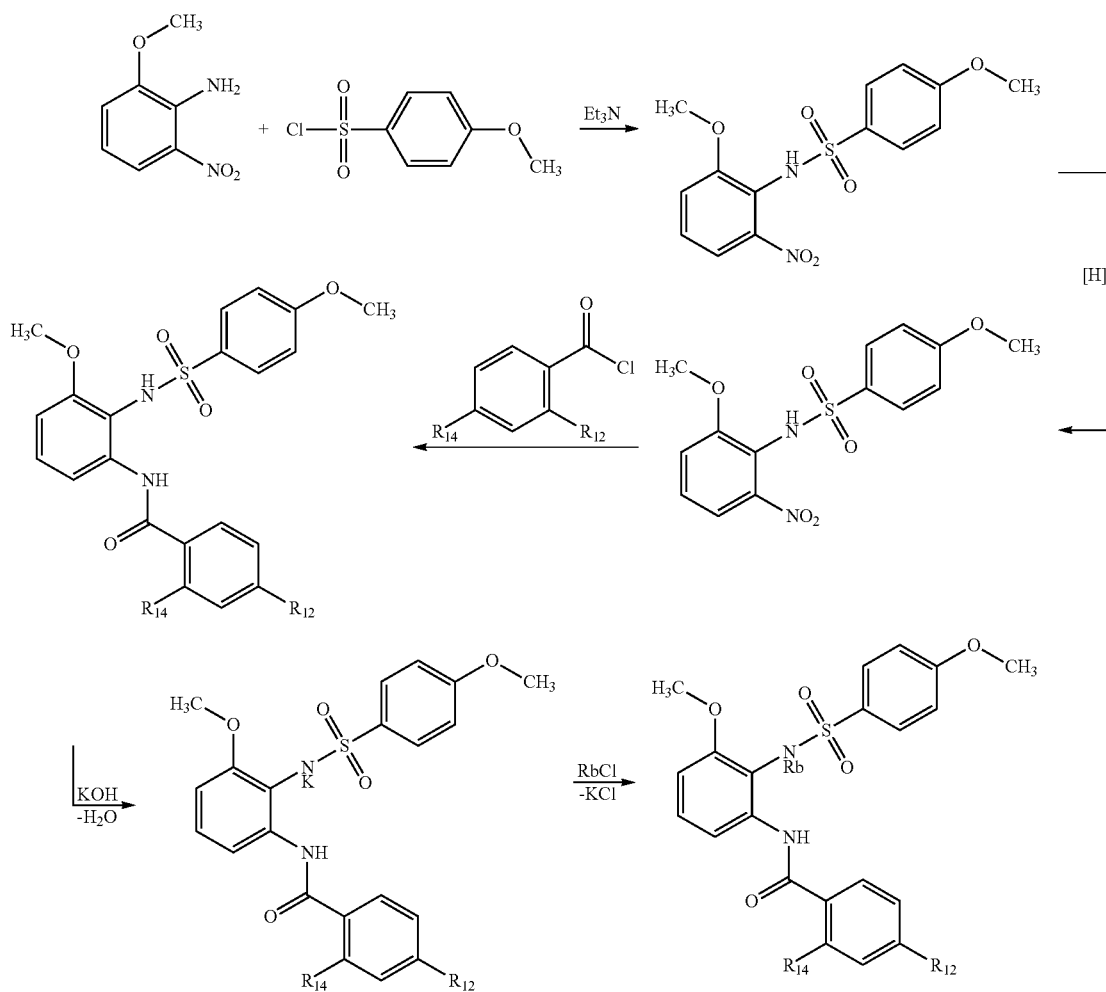

The invention claimed is:

1. A method of treating cancer comprising administering a composition comprising a compound of the following formula:

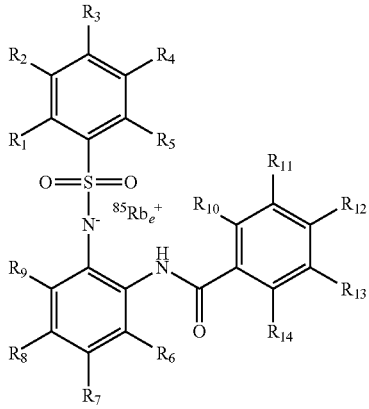

Formula 1 wherein each of $R_1$ through $R_{14}$ is independently selected from H, OH, F, Cl, Br, I, $C_1$-$C_6$ alkyl, $C_1$-$C_6$ alkoxy, and $NO_2$ and the $^{85}Rb_e$ is at least 90% $^{85}Rb$, to a patient in need thereof, wherein the cancer is melanoma.

2. The method of claim 1, further comprising administering to the patient a conventional form of cancer therapy within 36 hours of administering the composition.

3. The method of claim 2, wherein the composition is administered about 24 hours prior to administering the conventional form of cancer therapy.

4. A method of treating cancer comprising administering a composition comprising a compound of the following formula:

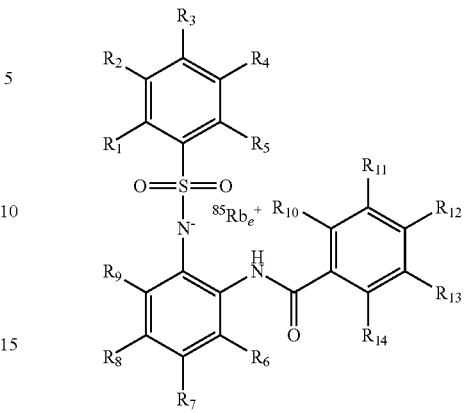

Formula 1 wherein each of $R_1$ through $R_{14}$ is independently selected from H, OH, F, Cl, Br, I, $C_1$-$C_6$ alkyl, $C_1$-$C_6$ alkoxy, and $NO_2$ and the $^{85}Rb_e$ is at least 90% $^{85}Rb$, to a patient in need thereof, wherein the composition is administered about 24 hours prior to administering the conventional form of cancer therapy and wherein the conventional form of cancer therapy comprises the administration of at least one antitumor drug, wherein the cancer is breast cancer or is melanoma.

5. The method of claim 4, wherein the at least one antitumor drug is selected from dacarbazine, doxorubicin, paclitaxel, vinorelbine and cisplatin.

6. The method of claim 1, wherein the compound is present in an amount equivalent to between 40 mg $^{85}Rb_e$ and 2400 mg $^{85}Rb_e$.

* * * * *